United States Patent
Bucala et al.

(10) Patent No.: US 10,765,739 B2
(45) Date of Patent: Sep. 8, 2020

(54) USE OF MIF AND MIF PATHWAY AGONISTS

(71) Applicant: Yale University, New Haven, CT (US)

(72) Inventors: Richard Bucala, Greenwich, CT (US); Lawrence H. Young, Woodbridge, CT (US)

(73) Assignee: Yale University, New Haven, CT (US)

( * ) Notice: Subject to any disclaimer, the term of this patent is extended or adjusted under 35 U.S.C. 154(b) by 177 days.

(21) Appl. No.: 15/648,956

(22) Filed: Jul. 13, 2017

(65) Prior Publication Data

US 2018/0008705 A1 Jan. 11, 2018

Related U.S. Application Data

(63) Continuation of application No. 13/751,887, filed on Jan. 28, 2013, now abandoned, which is a continuation of application No. 12/083,131, filed as application No. PCT/US2006/039315 on Oct. 6, 2006, now abandoned.

(51) Int. Cl.
| | |
|---|---|
| *C12N 15/62* | (2006.01) |
| *A61K 39/395* | (2006.01) |
| *C07K 14/52* | (2006.01) |
| *C12Q 1/6883* | (2018.01) |
| *A61K 31/7088* | (2006.01) |

(52) U.S. Cl.
CPC ...... *A61K 39/3955* (2013.01); *A61K 31/7088* (2013.01); *C07K 14/52* (2013.01); *C12Q 1/6883* (2013.01); *C12Q 2600/106* (2013.01); *C12Q 2600/156* (2013.01); *C12Q 2600/158* (2013.01); *C12Q 2600/166* (2013.01)

(58) Field of Classification Search
CPC .................................................. A61K 39/3955
See application file for complete search history.

(56) References Cited

U.S. PATENT DOCUMENTS

| | | |
|---|---|---|
| 2002/0150958 A1 | 10/2002 | Jung |
| 2003/0013122 A1 | 1/2003 | Bucala |
| 2012/0004261 A1 | 1/2012 | Jorgensen |
| 2012/0040974 A1 | 2/2012 | Jorgensen |

FOREIGN PATENT DOCUMENTS

| | | | | |
|---|---|---|---|---|
| WO | WO03/065979 | * | 8/2003 | |
| WO | 2004050898 A2 | | 6/2004 | |
| WO | 2005065328 A2 | | 7/2005 | |
| WO | 2007044622 | | 4/2007 | |
| WO | WO2007/044622 | * | 4/2007 | ............... C12N 9/12 |

OTHER PUBLICATIONS

Atsumi Toshiya et al: 'A role for macrophage migration inhibitory factor in the regulation of AMPK phosphorylation and insulin signal transduction.' Diabetes, vol. 52, No. Supplement 1, 2003, p. A297, XP009079318 & 63rd Scientific Sessions of the American Diabetes Association; New Orleans, LA, USA; Jun. 13-17, 2003 ISSN: 0012-1797.
Barton et al., "Macrophage migration inhibitory factor (MIF) gene polymorphism is associated with susceptibility to but not severity of inflammatory polyarthritis." 2003, Genes and Immunity, 4:487-491.
Shimizu et al., "Promoter region polymorphism of macrophage migration inhibitory factor is strong risk factor for young onset of extensive alopecia areata." 2005, Genes and Immunity, 6:285-289.
Radstake et al., "Correlation of rheumatoid arthritis severity with the genetic functional variants and circulating levels of macrophage migration inhibitory factor." 2005, Arthritis and Rheumatism, 52(10):3020-3029.
Meyer-Siegler et al., "Inhibition of macrophage migration inhibitory factor decreases proliferation and cytokine expression in bladder cancer cells." 2004, BMC Cancer, 4:34.
Young et al., "AMP-activated protein kinase: a key stress signaling pathway in the heart." 2005, Trends in Cardiovascular Medicine, 15(3): 110-118.
Benigni et al., 'The proinflammatory mediator macrophage migration inhibitory factor induces glucose catabolism in muscle.' 2000, J Clin Invest, 106(10): 1291-1300.
Kemp et al., "AMP-activated protein kinase, super metabolic regulator." 2003, Biochemical Society Transactions, 31:162-168.
Yu Tim Y et al: "Mice with deletion of macrophage migration inhibitory factor (MIF) develop insulin resistance due to reduced glucose uptake in white adipose tissue" Diabetes, vol. 54, No. Suppl. 1, Jun. 14, 2005 (Jun. 14, 2005), p. A475, XP009079316 & 65th Annual Meeting of the American-Diabetes-Association; San Diego, CA, USA; Jun. 10-14, 2005 ISSN: 0012-1797.
Miller Edward J et al: 'Macrophage migration inhibitory factor in the ischemic heart: Activation of AMP-activated protein kinase, stimulation of glucose transport, and prevention of cardiac dysfunction' Circulation, vol. 112, No. 17, Suppl. S, Oct. 2005 (Oct. 2005), p. U83, XP009079319; 78th Annual Scientific Session of the American-Heart-Association; Dallas, TX, USA; Nov. 13-16, 2005 ISSN: 0009-7322.
Weiseret al (PNAS. 1989; 86(19): 7522-7526).
Mitchell et al (PNAS. 2002; 99(1): 345-350).
Wang et al (Stroke. 2005; 36: 613-618 [published online before Feb. 3, 2005]).
Notice of Abandonment for application 12083131 (2013) (1 page).
Baron et al., "Dual mechanisms regulating AMPK kinase action in the ischemic heart." 2005, Circ Res, 96:337-45.
Meyer-Siegler et al., "Substance P induced changes in CD74 and CD44 in the rat bladder." 2005, J Urol, 173(2):615-620.

* cited by examiner

*Primary Examiner* — Scott Long
(74) *Attorney, Agent, or Firm* — Riverside Law LLP

(57) ABSTRACT

The present invention relates to novel methods and compositions for increasing AMPK activity and glucose uptake comprising administering a macrophage migration inhibitory factor (MIF) pathway agonist in a subject in need thereof. The invention also relates to methods for selecting a subject for treatment with an agonist of MIF, identifying a subject at risk for developing a condition in which increased AMPK activity is desirable, and for predicting whether a subject is susceptible to a condition in which increased AMPK activity is desirable.

2 Claims, 14 Drawing Sheets

Specification includes a Sequence Listing.

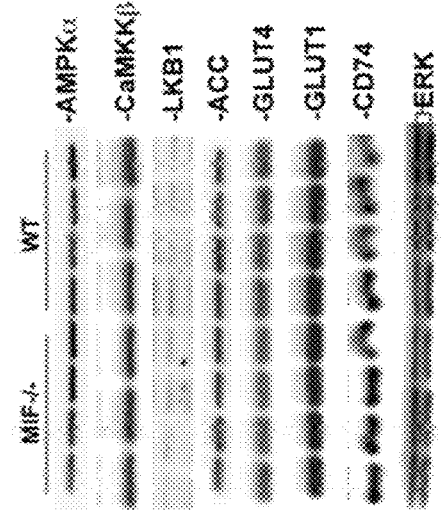
FIG. 5B
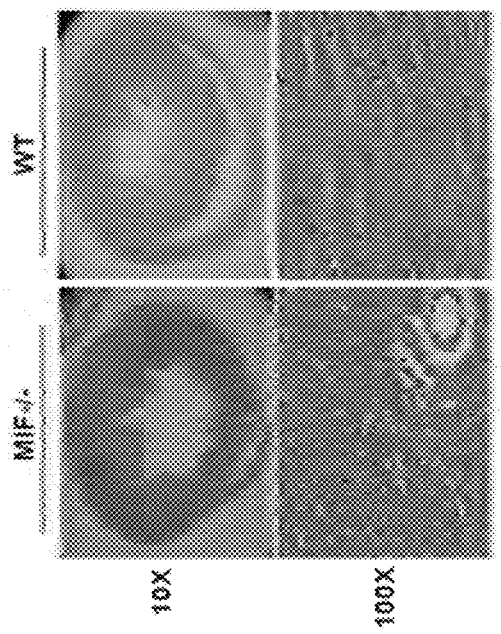
FIG. 5D
FIG. 5A
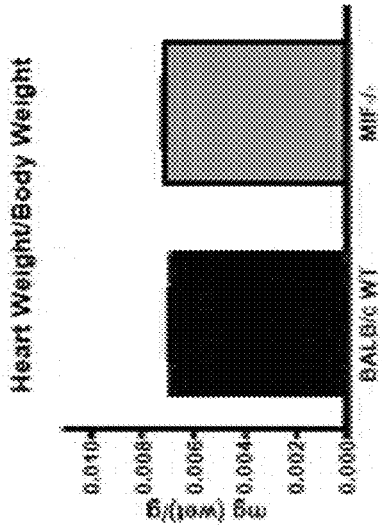
FIG. 5C

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Chemically Synthesized

<400> SEQUENCE: 1
cattcattca ttcattcatt                                        20

<210> SEQ ID NO 2
<211> LENGTH: 24
<212> TYPE: DNA
<213> ORGANISM: Artificial sequence

```
<220> FEATURE:
<223> OTHER INFORMATION: Chemically Synthesized

<400> SEQUENCE: 2
cattcattca ttcattcatt catt                                          24

<210> SEQ ID NO 3
<211> LENGTH: 28
<212> TYPE: DNA
<213> ORGANISM: Artificial sequence
<220> FEATURE:
<223> OTHER INFORMATION: Chemically Synthesized

<400> SEQUENCE: 3
cattcattca ttcattcatt cattcatt                                      28

<210> SEQ ID NO 4
<211> LENGTH: 32
<212> TYPE: DNA
<213> ORGANISM: Artificial sequence
<220> FEATURE:
<223> OTHER INFORMATION: Chemically Synthesized

<400> SEQUENCE: 4
cattcattca ttcattcatt cattcattca tt                                 32
```

USE OF MIF AND MIF PATHWAY AGONISTS

CROSS-REFERENCE TO RELATED APPLICATIONS

This application is a continuation of U.S. patent application Ser. No. 13/751,887, filed Jan. 28, 2013, which is a continuation of U.S. patent application Ser. No. 12/083,131, filed Apr. 3, 2008, which is a U.S. national stage filing under 35 U.S.C. § 371 of International Application No. PCT/US2006/039315, filed on Oct. 6, 2006, which claims priority under 35 U.S.C. § 119(e) from U.S. Provisional Patent Application No. 60/725,146, filed Oct. 7, 2005 and U.S. Provisional Patent Application No. 61/740,422, filed Nov. 29, 2005, all of which are herein incorporated by reference in their entirety.

STATEMENT REGARDING FEDERALLY-SPONSORED RESEARCH OR DEVELOPMENT

This invention was made with government support under HL063811 and AI042310 awarded by National Institutes of Health. The government has certain rights in the invention.

BACKGROUND OF THE INVENTION

Glucose uptake by cells is a critical process for maintaining cellular energy levels and ultimately, for tissue function and integrity. Increased glucose uptake has been shown to be cytoprotective in a number of settings. Increasing cellular glucose uptake also is advantageous in some metabolic conditions characterized by impaired glucose transport and in organs and tissues that have high energy requirements. An understanding of the mechanisms and pathways involved in cellular glucose uptake, thus, may permit the development of means for modulating the uptake process.

An important regulator of both glycolysis and glucose uptake in striated muscle is the AMP-activated protein kinase (AMPK). AMPK is a serine-threonine protein kinase that senses the cellular energy state, effecting multiple metabolic and non-metabolic pathways to increase cellular ATP production while also limiting energy consuming pathways (Young et. al., *Trends Cardiovase Med* 15, 110 (2005)). AMPK is regulated allosterically via AMP binding to its gamma regulatory subunit and by phosphorylation of Thr172 in the activating domain of the catalytic alpha subunit by upstream kinases, including LKB1 and CaMKKβ (Baron et al., *Circ Res* (2005)).

AMPK is activated under conditions that lead to inadequate blood flow and associated tissue ischemia, such as coronary artery disease. In the heart, AMPK directly stimulates PFK-2 activity and glycolysis (Marsin et al., *Curr Biol* 10, 1247 (2000)), induces GLUT4 translocation and increases ischemic glucose uptake preserves high energy phosphate content and limits myocardial injury and apoptosis (Russell, 3rd et al., *J Clin Invest* 114, 495 (2004)). AMPK also stimulates skeletal muscle glucose transport (Bergeron et al AJP 1999) through mechanism that is independent of the insulin signaling pathway; thus AMPK provides a target for the therapy of people with type 2 diabetes in whom the insulin stimulated pathway of glucose transport is impaired, leading to hyperglycemia. Since vascular disease, including coronary artery disease, peripheral arterial disease and cerebrovacular disease are highly prevalent in type 2 diabetes, AMPK represents a highly desirable target for both the treatment of the metabolic derangements of type 2 diabetes and the prevention of ischemic injury in these patients.

Accordingly, there is a critical need for methods and compositions for preventing cellular and tissue injury resulting from tissue ischemia. In particular, there is a need for methods and compositions for increasing cellular glucose uptake and preventing the depletion of energy stores during energetic stress associated with ischemia utilizing the AMPK pathway.

SUMMARY OF THE INVENTION

The present invention provides novel methods for increasing AMPK activity and glucose uptake comprising administering MIF or a MIF pathway agonist (a "MIF agonist") in a subject in need thereof.

In one embodiment, the invention provides a method of selecting a subject for treatment with a MIF agonist, wherein the subject has, or is at risk of developing, a condition in which increased AMPK activity is desirable, comprising genotyping the subject for the presence of a polymorphism associated with decreased MIF expression, wherein a subject having a polymorphism associated with decreased MIF expression is selected for treatment with a MIF agonist.

In another embodiment, the invention provides a method of identifying a subject at risk of developing a condition in which increased AMPK activity is desirable, comprising genotyping the subject for the presence of a polymorphism associated with decreased MIF expression, wherein a subject having a polymorphism associated decreased MIF expression is at an increased risk of developing a condition in which increased AMPK activity is desirable.

In another embodiment, the invention provides a method of predicting the severity of a condition in which increased AMPK activity is desirable in a subject, comprising genotyping the subject for the presence of a polymorphism associated with decreased MIF expression, wherein a subject having a polymorphism associated with decreased MIF expression is at an increased risk of developing a more severe condition in which increased AMPK activity is desirable.

In other embodiments, the invention provides a method of predicting whether a subject is susceptible to a condition in which increased AMPK activity is desirable, comprising genotyping a subject for the presence of a polymorphism associated with decreased MIF expression, wherein a subject having a polymorphism associated with decreased MIF expression is more susceptible to the condition.

Polymorphisms associated with decreased MIF expression include: the presence of five, or fewer than five, CATT repeats in the −794 region of one or both alleles of the MIF gene or the presence of guanine at position −173 of one or both alleles of the MIF gene. In one embodiment, a polymorphism associated with decreased MIF expression is the presence of five CATT repeats in the −794 region of both alleles of the MIF gene. In another embodiment, a polymorphism associated with decreased MIF expression is the presence of five CATT repeats in the −794 region of both alleles of the MIF gene and the presence of guanine at position −173 of one or both alleles of the MIF gene.

Polymorphisms associated with increased MIF expression include: the presence of six or more CATT repeats in the −794 region of both alleles of the MIF gene or the presence of a non-guanine nucleotide at position −173 of both alleles of the MIF gene.

In certain embodiments, a method of genotyping a subject for the presence of a polymorphism associated with decreased MIF expression comprises contacting a sample obtained from the subject with a polynucleotide probe that hybridizes specifically to a sequence comprising a polymorphism associated with decreased MIF expression determining whether hybridization occurs. Hybridization indicates whether the subject comprises a polymorphism associated with decreased MIF expression, thereby genotyping the subject for the presence of a polymorphism associated with decreased MIF expression. In other embodiments, the method further comprises contacting the sample with a control polynucleotide probe, wherein the control polynucleotide probe does not hybridize specifically to a sequence comprising a polymorphism associated with decreased MIF expression. Hybridization of the polynucleotide probe but not the control polynucleotide probe indicates the presence of a MIF polymorphism associated with decreased MIF expression.

In other embodiments, a method of genotyping a subject for the presence of a polymorphism associated with decreased MIF expression comprises: (a) contacting a sample obtained from the subject with a pair of amplification primers, wherein the primers are capable of amplifying a portion of the MIF promoter comprising a polymorphism associated with decreased MIF expression; (b) amplifying DNA in the sample, thereby producing amplified DNA; and, (c) determining whether the amplified DNA comprises a polymorphism associated with decreased MIF expression, thereby genotyping the subject for the presence of a polymorphism associated with decreased MIF expression. In certain embodiments, the method comprises sequencing the amplified DNA.

In another embodiment, the invention provides a method of treating or preventing a condition in which increased AMPK activity is desirable, comprising administering to a subject in need thereof a MIF agonist. In some embodiments, a MIF agonist is administered to a subject having a polymorphism associated with decreased MIF expression. In other embodiments, a subject having a polymorphism associated with decreased MIF expression is administered a greater dose or amount of a MIF agonist than a patient having a polymorphism associated with high MIF expression.

In some embodiments, a method of treating or preventing a condition in which increased AMPK activity is desirable further comprises a therapeutic regimen that includes one or more additional treatment modalities.

In another embodiment, the invention provides a method of increasing phosphorylation of threonine at position 172 of the AMPK protein in a cell, comprising administering a MIF agonist to a subject in need thereof.

In another embodiment, the invention provides a method of increasing AMPK-mediated GLUT4 activation in a cell, comprising administering a MIF agonist to a subject in need thereof.

In another embodiment, the invention provides a method of increasing uptake of AMPK-mediated glucose into a cell, comprising administering a MIF agonist to a subject in need thereof.

In another embodiment, the invention provides a method of increasing AMPK-mediated glycogen synthesis in a cell, comprising administering a MIF agonist to a subject in need thereof.

In yet another embodiment, the invention provides a method of stimulating AMPK-mediated PFK-2 activity in a cell, comprising administering a MIF agonist to a subject in need thereof.

In other embodiments, the invention provides a method of increasing AMPK-mediated glycolysis in a cell, comprising administering a MIF agonist to a subject in need thereof.

In some embodiments, the invention provides a composition comprising one or more MIF agonists and at least one AMPK agonist. In other embodiments, the invention provides a composition comprising one or more MIF agonists and at least one additional therapeutic agent.

Additional therapeutic agents may include, for example, compounds for treating a subject having, or at risk of developing, ischemia or conditions related to ischemia, organ transplant surgery, or conditions in which AMPK-mediated glucose uptake is desirable. In a specific embodiment, a condition in which increased AMPK activity is desirable is type 2 diabetes.

Conditions in which increased AMPK activity is desirable include, for example, hypoxia, especially hypoxia resulting from tissue ischemia. The ischemia may be from any cause including acute coronary syndromes such as myocardial infarction, coronary revascularization (such as coronary bypass surgery and coronary angioplastyistent placement), stroke, renal, retinal, mesenteric or limb ischemia due to vascular occlusion, organ transplant surgery (for maintaining viability and function of the transplanted organ), ischemia associated with vascular surgery, including hypothermic arrest and vascular cross-clamping. Other conditions in which increased AMPK activity is desirable include, for example, conditions in which AMPK-mediated glucose uptake is desirable. In a specific embodiment, a condition in which increased AMPK activity is desirable is type 2 diabetes.

A MIF agonist may be, for example, a MIF polypeptide, a CD74 agonist, a CD44 agonist, a bivalent antibody that increases the interaction between MIF, CD74 and CD44, a bivalent antibody that increases the interaction between MIF and CD74, or a bivalent antibody that increases the interaction between CD74 and CD44. A MIF agonist may also include a polynucleotide or cDNA molecule that encodes any of the above proteins, including a MIF polypeptide.

BRIEF DESCRIPTION OF THE DRAWINGS

FIG. 1A: Top. AMPK alpha subunit (α1 or α2) isoform-specific kinase activity from rat heart left ventricular papillary muscles incubated in either oxygenated (100% $O_2$) or hypoxic (100% $N_2$) buffer for 30 minutes (n=3 per group, *P<0.01 vs. isoform control and between hypoxic α1 and α2). Bottom. Representative anti-phospho Thr172 AMPK immunoblots from papillary muscle homogenates. FIG. 1B: Papillary muscle MIF production; incubation buffer was sampled every 5 minutes via ELISA during either control (oxygenated) or hypoxic (30 minutes) incubation (n=3 per group, P=0.03 ANOVA). FIGS. 1C and 1D): Anti phospho Thr172 AMPK immunoblot densitometry, representative immunoblots, and papillary muscle 2-deoxy-D-[1-$^3$H]glucose uptake from papillary muscles incubated in hypoxic (100% $N_2$) buffer for 30 minutes, with or without pre-incubation with anti-MIF antibody or non-immune IgG (both 100 ug/ml) (n=3 per group, *P<0.05 vs. control, # P<0.05 vs. Hypoxic alone). FIG. 1E: Anti-phospho Thr172 AMPK representative immunoblots and immunoblot densitometry from normoxic papillary muscles incubated with rMIF (0-400 ng/ml) for 60 minutes (n=3-4/condition, *P<0.02 vs. control). FIG. 1F: Anti-phospho Thr172 AMPK immunoblot densitometry from normoxic papillary muscles incubated with rMIF (400 ng/ml) for 0-120 minutes (n=3-4/condition, *P<0.05 vs. control). FIG. 1G: Papillary muscle 2-deoxy-D-[1-$^3$H]glucose uptake during incubation with rMIF (0-800 ng/ml) for 60 minutes (n=6-8 per group, overall P<0.0001, *P<0.05 vs. control. FIG. 1H: Cell-surface GLUT4 representative immunoblots and immunoblot densitometry measured using the cell-impermeant exofacial photolabel, bio-LC-ATB-BGPA, after papillary muscle incubation with rMIF (400 ng/ml) for 60 minutes (n=4, *P<0.001).

FIG. 2A: (top) Representative anti-MIF immunohistochemistry (40×) from formalin-fixed, paraffin-embedded sections of WT and MIF−/− hearts following control perfusion. Primary antibody either anti-MIF or non-specific rabbit IgG developed with DAB and counterstained with hematoxylin. (bottom) Whole-heart lysates from WT and MIF−/− hearts immunoblotted for MIF. Total AMPK was used as a loading control. FIG. 2B: (left) Coronary effluent [MIF] measured by ELISA from WT hearts during both control perfusion or ischemia/reperfusion. No MIF was detected in MIF−/− hearts' coronary effluent (n=3, P=0.01). (right) Whole-heart lysates from WT hearts immunoblotted for MIF after control perfusion or ischemia/reperfusion (n=3, *P=0.003).

FIG. 3A: Anti-phospho Thr172 AMPK immunoblot densitometry, representative immunoblots. (left) and isoform-specific kinase activity. (right) from tissue lysates from MIF−/− or WT hearts subjected to either control perfusion or ischemia/reperfusion (immunoblots: n=4 per group, *P<0.05 WT ischemia vs. MIF−/− ischemia, # P<0.05 ischemia vs. control; kinase activity: n=3 per group). FIG. 3B: Cardiac glucose uptake determined from the production of tritiated water from [2-$^3$H]glucose (n=5 for each genotype, *P=0.01 vs. WT basal, # P—0.04 vs. MIF−/− reperfusion). FIG. 3C: Cardiac rate pressure product (heart rate×left ventricular developed pressure) during baseline perfusion period and after 15 minutes of global, no-flow ischemia (n=12 for each genotype during basal perfusion, 5 for each genotype during post-ischemic reperfusion, P=0.03 by repeated measures ANOVA during reperfusion).

FIG. 4A: Fibroblast incubation media [MIF] measured by ELISA from human fibroblasts subjected to either control incubation (95% room air; 5% $CO_2$) or hypoxia (95% $N_2$; 5% $CO_2$) for 9 hours, expressed relative to cellular lysate protein concentration (*P=0.03 vs. 5/5 control, # P=0.05 vs 5/5 9-hours of hypoxia, & P=0.03 vs. 5/5 control). Data combined from fibroblasts with MIF promoter −794 $CATT_{5-8}$ tetranucleotide repeat polymorphisms of both 5-CATT repeat alleles ('5/5' genotype) or any combination of 6, 7, or 8-CATT repeat alleles ('non-5/5' genotype) (5/5n=3, non-5/5 n=4). FIG. 4B: Anti-phospho Thr172 AMPK immunoblots from human fibroblasts subjected to control or hypoxic incubation, with or without the addition of 10 ng/ml rMIF. (expressed relative to total AMPK, experiments run in triplicate, *P=0.01 control vs. 9-hours of hypoxia, # P=0.04 5/5 vs. non-5/5 9-hours of hypoxia).

FIGS. 5A-5D show the characterization of the cardiac phenotype of MIF−/− mice. FIG. 5A: Heart weight (wet) and body weight measured from age-matched WT and MIF−/− mice at 12-20 weeks of age (n=13/group). FIG. 5B: Transthoracic 2-dimensional echocardiographic images of the left ventricle were obtained in the short axis using a 15 MHz probe on a Phillips Sonos 5500 machine. Mice were lightly anesthetized with inhaled isoflurane. Measurements were made in triplicate by a blinded observer (n=4 per group). FIG. 5C: Representative hematoxylin/eosin stained sections of formalin-fixed, paraffin-embedded hearts (n=2-4 per group). FIG. 5D: Immunoblots of total AMPK alpha, CaMKKβ, LKB1, ACC, GLUT4, GLUT1, and MIF from WT and MIF−/− hearts (n=3-4 per group)

DETAILED DESCRIPTION OF THE INVENTION

Figure 1A:
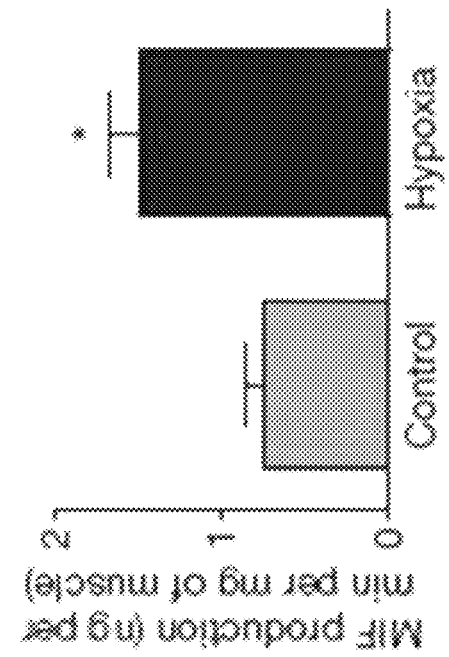
FIGS. 1A-1H are graphs showing MIF-associated AMPK signaling in isolated papillary muscles.
Figure 1B:
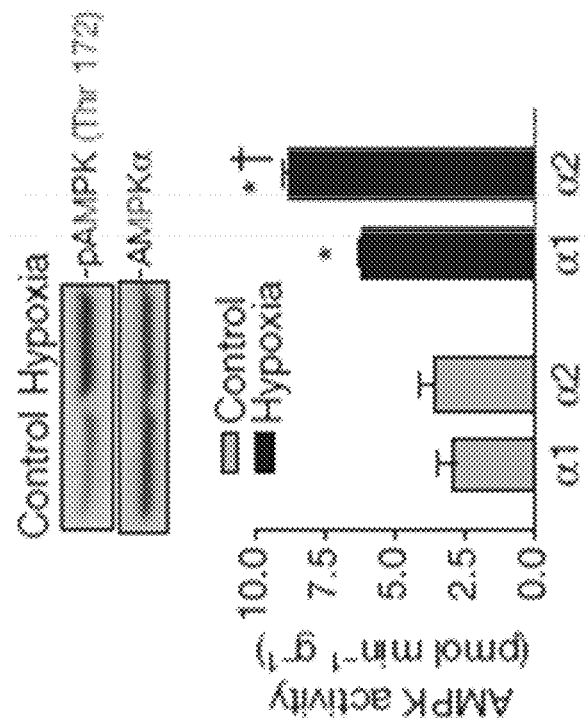

The present invention provides novel methods for increasing AMPK activity and glucose uptake comprising administering MIF or a MIF pathway agonist (a "MIF agonist") in a subject in need thereof.

The methods and compositions of the present invention are useful to treat or prevent conditions in which AMPK-mediated glucose uptake is desirable. Such conditions include hypoxia, especially hypoxia resulting from tissue ischemia. The ischemia may be from any cause including acute coronary syndromes such as myocardial infarction, coronary revascularization (such as coronary bypass surgery and coronary angioplasty/stent placement), stroke, renal, retinal, mesenteric or limb ischemia due to vascular occlusion, organ transplant surgery (for maintaining viability and function of the transplanted organ), ischemia associated with vascular surgery, including hypothermic arrest and vascular cross-clamping.

Where tissue ischemia is anticipated to occur in a subject, such as a subject about to undergo a surgical procedure involving the interruption or the substantial reduction of blood flow to a tissue or organ, or where the subject is at risk for an ischemic event, the methods and compositions of the present invention also are useful to pretreat the subject with one or more MIF agonists to increase AMPK activation and glucose uptake prior to the onset of anticipated hypoxic or ischemic insult. For example, prior to coronary revascularization, such as coronary bypass surgery and coronary angioplasty/stent placement. The administration of one or more MIF agonists also is advantageous prior to vascular surgery including hypothermic arrest and vascular cross-clamping. In addition, patients with symptoms or syndromes indicating imminent risk for severe ischemia may benefit from the administration of MIF agonists. For example, patients with unstable angina, who are at risk for heart attack or those with transient ischemic attack, who are at risk for stroke.

The methods and compositions of the invention also are useful in patients suffering from a metabolic condition in which it is advantageous to increase cellular glucose uptake, for example, in patients with type II diabetes.

Subjects who may benefit from increased AMPK activity, e.g., to prevent cellular and tissue injury due to tissue ischemia, hypoxia, or other related conditions, or to increase glucose uptake, include but are not limited to subjects who carry common polymorphisms in their MIF genes that are associated with reduced MIF expression.

It is a further discovery of the present invention that differential MIF expression governed by such polymorphisms has consequences in stress signaling, specifically reducing hypoxic AMPK signaling that can be "rescued" by the administration of MIF.

Patients with low-MIF expression polymorphisms in whom it would be advantageous to increase AMPK signaling and cellular glucose uptake, thus, may particularly benefit from treatment with a MIF agonist. Accordingly, the invention provides methods for identifying candidates for treatment with one or more MIF agonists to increase AMPK activation and for predicting therapeutic response to such treatment by genotyping them to detect the presence of a polymorphism associated with reduced MIF expression.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof.

At used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The terms "comprise" and "comprising" are used in the inclusive, open sense, meaning that additional elements may be included.

The term "including" is used to mean "including but not limited to". "Including" and "including but not limited to" are used interchangeably.

The term "agent" is used herein to denote a chemical compound, a mixture of chemical compounds, a biological macromolecule (such as a nucleic acid, an antibody, a protein or portion thereof, e.g., a peptide), or an extract made from biological materials such, as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject. Agents can comprise, for example, drugs, metabolites, intermediates, cofactors, transition state analogs, ions, metals, toxins and natural and synthetic polymers (e.g., proteins, peptides, nucleic acids, polysaccharides, glycoproteins, hormones, receptors and cell surfaces such as cell walls and cell membranes. Agents may also comprise alcohols, alkyl halides, amines, amides, esters, aldehydes, ethers and other classes of organic agents.

A "patient", "subject", or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, locl (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a nonnatural arrangement.

The term "prophylactic" or "therapeutic" treatment is art-recognized and refers to administration of a drug and/or a non-drug modality (such as, for example, surgery, radiation, electrotherapy, diet, nutrition or exercise) to a patient. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

As used herein, the term "MIF" or "MIF polypeptide" refers to macrophage migration inhibitory factor or active fragments thereof. Accession number EMBL Z23063 describes the nucleic acid sequence encoding human MIF (Bernhagen et al., *Biochemistry* 33:14144-14155 (1994)). An active fragment of MIF may comprise a fragment or a portion of the MIF protein encoding the tautomerase enzymatic activity of MIF or a fragment that is capable of binding CD74.

As used herein a "MIF agonist" refers to any agent that mimics, activates, stimulates, potentiates or increases the biological activity of MIF. A MIF agonist may be MIF or a fragment thereof; an agent that mimics MIF (such as a small molecule); an agent that increases or enhances the expression of MIF, CD74 or CD44; an agent that enhances the binding of MIF to CD74; an agent than enhances the interaction between CD74 and CD44 (including, without limitation, a bivalent agent).

As used herein, the "biological function of MIF" refers to the ability of MIF to carry out one or more of the biological functions of MIF including, without limitation, sustaining immune cell survival or activation, promoting cytokine promotion, down-regulating CCR5, binding to CD74, activating AMPK signaling, activating MAP kinase signaling (e.g., ERK1/2, JNK, and SAPK MAP kinase signaling), inhibiting p53, acting as a tautomerase, and/or acting as a thiol reductase.

As used herein, the term "treating" refers to preventing, slowing, delaying, stopping or reversing the progression of a condition.

As used herein, "a polymorphism associated with altered MIF expression" refers to any polymorphisms in the MIF gene that correlate with increased or expression of the MIF gene, including without limitation; a single nucleotide polymorphism (G/C) at position −173 of the MIF promoter or the presence of five, six, seven or eight CATT repeats at position in the −794 region of the MIF promoter.

As used herein, "a polymorphism associated with reduced MIF expression" refers to the presence of a guanine (G) at position −173 of one or both alleles of the MIF gene or the presence of five, or fewer than five, CATT boxes at position in the −794 region of one or both alleles of the MIF gene. (The positions of the MIF promoter are defined by reference to the nucleic acid sequence disclosed in EMBL Z23063.)

As used herein, "a polymorphism associated with increased MIF expression" refers to the presence of a cytosine (C) at position −173 of both alleles of the MIF gene or the presence of six or more CATT boxes at position in the −794 region of both alleles of the MIF gene. (The positions of the MIF promoter are defined by reference to the nucleic acid sequence disclosed in EMBL Z23063.)

Each subject has two alleles corresponding to the MIF gene. As used herein, "a subject having a polymorphism associated with reduced MIF expression" refers to a subject that has a G at position −173 of the MIF gene in one or both alleles or that has five, or fewer than five, CATT repeats in the −794 region of the MIF gene is one or both alleles. As used herein, "a subject having a polymorphism associated with increased MIF expression" refers to a subject that has a polymorphism associated with increased MIF expression in both of alleles of the MIF gene.

As used herein "higher risk" or "increased risk" refers to a statistically higher frequency of occurrence of the disease or condition. As used herein "lower risk" or "decreased risk" refers to a statistically lower frequency of occurrence of the disease or condition.

As used herein, the term "severity" of a condition, refers to the seriousness, degree or state of a disease or condition. For example, a condition may be characterized as mild, moderate or severe. A person of skill in the art would be able to determine or assess the severity of a particular condition. For example, the severity of a condition may be determined by comparing the likelihood or length of survival of a subject having a condition with the likelihood or length of survival in other subjects having the same condition. In another embodiment, the severity of a condition may be determined by comparing the symptoms of the condition in a subject having a condition with the severity of the symptoms in other subjects having the same condition.

As used herein, the term "therapeutically effective amount" refers to the amount of a MIF agonist (isolated or recombinantly produced), or a composition comprising a MIF agonist, that is in sufficient quantities to increase AMPK activity, increase glucose uptake and/or delay, reduce or prevent cellular tissue injury from hypoxia, including from tissue ischemia. For example, an effective amount is sufficient to delay, slow, or prevent the onset or progression of a condition associated with impaired insulin-mediated glucose uptake such as in type 2 diabetes.

As used herein, the terms "isolated" and "purified," when used in relation to a nucleic acid, protein or other compound, refer to the separation of the nucleic acid, protein or other compound from at least one contaminant with which it is ordinarily associated in its natural source.

Methods of Treating Diseases Associated with Reduced MIF Expression

In certain embodiments, the invention features methods of increasing AMPK activity and glucose uptake in a subject in need thereof, comprising administering to a subject in need thereof a therapeutically effective amount of one or more MIF agonists. In some embodiments, the invention comprises administering to a subject having, or at risk of developing, tissue ischemia. In some embodiments, the subject suffers from a condition in which augmenting AMPK activity provides favorable metabolic effects. In some embodiments the AMPK activation provides protective effects to prevent cellular tissue injury. In another embodiment, the invention comprises administering to a subject having, or at risk of developing, type 2 diabetes.

Conditions that are associated with a need for increasing AMPK activity include without conditions that are associated with inadequate blood flow. Such conditions include, without limitation, myocardial ischemia and infarction, transient ischemic attack, stroke, hypoxia, tachycardia, atherosclerosis, hypotension, tissue ischemia from thromboembolism, compression of blood vessels, foreign bodies in the blood circulation, sickle cell disease, cerebrovascular injury and peripheral artery occlusive disease.

The methods and compositions described herein also can be used prior to treatments or conditions that may result in inadequate blood flow. Where ischemia is anticipated in a subject with reduced MIF expression, it is particularly advantageous to pretreat the subject with a MIF agonist. For example, the methods and compositions described herein may be useful for organ preservation or prior to or during organ transplantation. Prophylactic treatment with a MIF agonist also is advantageous in subjects suffering from conditions such as unstable angina, transient ischemic attack and the like, in which reduced blood flow and/or tissue ischemia is anticipated.

In another embodiment, the methods and compositions described herein can be used in connection with type 2 diabetes or other diseases or conditions that may benefit from increased glucose uptake into the cells.

The methods and compositions described herein are useful for increasing AMPK activity in any cells, tissues, or organs of the body. For example, the methods and compositions described herein may be used to treat conditions that occur in cardial and skeletal muscle, the heart, brain, liver, kidney, and lungs. In particular, the methods and compositions described herein may be used to prevent cardiac injury and dysfunction ischemia and to prevent loss of viability or function of organs for transplant.

In another embodiment, the methods and compositions described herein can be used in connection with type 2 diabetes or other diseases or conditions that may benefit from increased glucose uptake into the cells, or where increased AMPK activation can delay or reduce adverse metabolic effects or tissue injury.

In various embodiments, MIF agonists can be, for example, drugs, metabolites, intermediates, cofactors, transition state analogs, ions, metals, toxins and natural and synthetic polymers (e.g., proteins, peptides, nucleic acids, polysaccharides, glycoproteins, hormones, receptors and cell surfaces such as cell walls and cell membranes. Agents may also comprise alcohols, alkyl halides, amines, amides, esters, aldehydes, ethers and other classes of organic agents. Exemplary MIF agonists are known in the art. Further, certain MIF agonists are described infra and supra.

In some embodiments the subjects early a MIF gene polymorphism that results in reduced MIF expression and/or activity.

Prognostic and Diagnostic Methods

In one aspect, the invention provides methods for identifying subjects in whom it would be particularly advantageous to administer one or more MIF agonists to increase AMPK activity. The methods comprise genotyping the subject for the presence of a polymorphism associated with reduced MIF expression.

Polymorphisms in the structure of the promoter region of the MIF gene are known to street the level of MIF expression (Baugh et al. (2002) *Genes Immun.* 3:170-176 and De Benedetti et al. (2003) *Arthritis & Rheum* 48:1398-1407).

A polymorphism associated with altered MIF expression may be any genetic alteration that modifies or correlates with the expression or activity of MIF. Polymorphisms associated with reduced MIF expression include, without limitation, the presence of five or fewer CATT repeats in the −794 region of one or both alleles of the MIF promoter, or a guanine at position −173 of one or both alleles of the MIF promoter. Polymorphisms associated with increased MIF expression include, without limitation, the presence of six, seven or eight CATT repeats in the −794 region of both alleles of the MIF promoter or the presence of a nucleotide other than guanine at position −173 of both alleles of the MIF promoter. In a specific embodiment, a polymorphism associated with increased MIF expression is the presence of cytosine (C) at position −173 of both alleles of the MIF gene. In general, the greater the number of CATT repeats present in the −794 region of the MIF promoter, the greater the expression and/or activity of MIF. The above polymorphisms are illustrative of polymorphisms that may be associated with altered MIF expression. Nevertheless, subjects in particular need of MIF agonist therapy include those with any polymorphism that results in reduced MIF expression or activity. As an illustrative embodiment, polymorphisms consisting of a G/A or G/T nucleotide change at position −173 of the MIF promoter may be associated with high or reduced MIF expression. In another illustrative embodiment, the presence of two, three, four, nine, ten, eleven or twelve or more CATT repeats in the −794 region of the MIF promoter may be associated with increased or decreased MIF expression. Methods of genotyping a subject for the presence of a polymorphism (including single nucleotide polymorphisms and microsatellite repeats) in a gene are well known and routinely used in the art. Exemplary methods of genotyping a subject for the presence of a polymorphism in the MIF gene are described below.

In one embodiment, the methods of the invention are useful for selecting a subject for treatment with a MIF agonist, wherein the subject is in need or may imminently be in need of increased AMPK activity. For example, the methods of the invention are useful for selecting a subject for treatment with a MIF agonist, wherein the subject has or is at risk of developing a condition associated with inadequate blood flow. Alternatively, the methods of the invention are useful for selecting a subject for treatment with a MIF agonist, wherein the subject has or is at risk of developing type 2 diabetes or any other condition that may benefit from increased glucose uptake into cells. Such methods comprise genotyping the subject to detect the presence of a polymorphism associated with reduced MIF expression, wherein a subject having a polymorphism associated with reduced MIF expression is identified as a candidate for treatment with a MIF agonist.

In other embodiments, genotyping subjects to identify reduced MIF expressers provides a means of predicting the potential severity of ischemic damage in a subject and for identifying subjects at particular risk for ischemia/hypoxia-related injury.

Genotyping Assays

Certain aspects of the invention comprise genotyping a subject for the presence of a polymorphism associated with reduced MIF expression. Any assay that permits detection of polymorphism in the MIF gene (which is used herein to include the MIF coding region and the MIF promoter region) may be used in the claimed methods. The preferred method for detecting a polymorphism will depend, in part, upon the molecular nature of the polymorphism. For example, certain methods may be amenable to the detection of insertions, deletions, substitutions, repeats, or single nucleotide polymorphisms (SNPs). Such assays are well known in the art and may encompass, for example, DNA sequencing, hybridization, ligation, or primer extension methods.

In one embodiment, geneotyping a subject may comprise contacting a sample obtained from the subject with a polynucleotide probe that hybridizes specifically to a sequence comprising a polymorphism associated with altered MIF expression, and, determining whether hybridization occurs. The polynucleotide probe can be engineered to hybridize specifically to a sequence comprising a polymorphism associated with reduced MIF expression, but not to a sequence comprising a polymorphism associated with increased MIF expression. Hybridization of the probe to the DNA in the sample indicates whether the subject comprises a polymorphism associated with reduced MIF expression. In certain embodiments, methods for genotyping a subject for the presence of a polymorphism that is associated with altered MIF expression further comprises contacting a sample obtained from the subject with a control polynucleotide probe. A control polynucleotide probe will not, for example, hybridize specifically to a sequence comprising a polymorphism associated with reduced MIF expression. The polynucleotide probe may comprise nucleotides that are fluorescently, radioactively, or chemically labeled to facilitate detection of hybridization.

Hybridization may be performed and detected by standard methods known in the art, such as by Northern blotting, Southern blotting, fluorescent in situ hybridization (FISH), or by hybridization to polynucleotides immobilized on a solid support, such as a DNA array or microarray. Array elements may comprise any polynucleotide, including genomic DNA, cDNA, synthetic DNA or other types of nucleic acid array elements.

In one embodiment, the probe is a DNA probe that is immobilized on a solid support, such as a DNA array or microarray. In one embodiment, the probe is from about 8 nucleotides to about 500 nucleotides.

In another embodiment, a subject is genotyped for the presence of a polymorphism associated with altered MIF expression by hybridization to a DNA array or microarray, by incorporation of blotinylated primers followed by avidin-enzyme conjugate detection, or by incorporation of $^{32}$P-labeled deoxynucleotide triphosphates, such as dCPT or dATP, into the target polynucleotides (e.g., a polynucleotide that may include a polymorphism that is associated with altered MIF expression). Hybridization may be detected, for example by measuring the intensity of the labeled probe remaining on a DNA array after washing.

Methods of detecting a polymorphism associated with reduced MIF expression may include amplification of a region of DNA that comprises a polymorphism that is associated with reduced MIF expression. Any method of amplification may be used. In one specific embodiment, a region of DNA comprising the variation is amplified by using polymerase chain reaction (PCR). PCR was initially described by Mullis (See e.g., U.S. Pat. Nos. 4,683,195 4,683,202, and 4,965,188, herein incorporated by reference), which describes a method for increasing the concentration of a region of DNA, in a mixture of genomic DNA, without cloning or purification. Other PCR methods may also be used for nucleic acid amplification, including but not limited to RT-PCR, quantitative PCR, real time PCR, Rapid Amplified Polymorphic DNA Analysis, Rapid Amplification of cDNA Ends (RACE), rolling circle amplification, or multiple displacement amplification. For example, polynucleotide primers that flank the MIF gene (including the MIF promoter) are combined with a DNA mixture. The mixture also includes the necessary amplification reagents (e.g., deoxyribonucleotide triphosphates, buffer, etc.) necessary for thermal cycling reaction. According to standard PCR methods, the mixture undergoes a series of denaturation, primer annealing, and polymerase extension steps to amplify the region of DNA that comprises a polymorphism that is associated with reduced MIF expression. The length of the amplified region of DNA is determined by the relative positions of the primers with respect to each other, and therefore, this length is a controllable parameter. For example, hybridization of the primers may occur such that the ends of the primers proximal to the variation are separated by 1 to 10,000 base pairs (e.g., 10 base pairs (bp) 50 bp, 200 bp, 500 bp, 1,000 bp, 2,500 bp, 5,000 bp, or 10,000 bp).

In other embodiments, methods for genotyping a subject for the presence of a polymorphism that is associated with reduced MIF expression comprise; (a) contacting a sample obtained from the subject with a pair of amplification primers, wherein said primers are capable of amplifying a portion of the MIF promoter comprising a polymorphism associated with reduced MIF expression; (b) amplifying DNA in the sample, thereby producing amplified DNA; and (c) determining whether the amplified DNA comprises a polymorphism associated with reduced MIF expression, thereby genotyping the subject for the presence of a polymorphism associated reduced MIF expression. The step of determining whether the amplified DNA comprises a polymorphism associated with reduced MIF expression can be carried out using any method known in the art and/or described herein. The method may further comprise sequencing the amplified DNA.

In one embodiment, the presence of a polymorphism associated with reduced MIF expression is detected and/or determined by DNA sequencing. Any of a variety of sequencing reactions known in the art can be used to directly sequence the allele. Examples of sequencing reactions include those based on techniques developed by Maxim and Gilbert ((1977) *Proc. Natl. Acad. Sci. USA* 74:560) or Sanger (Sanger et al (1977) *Proc. Nat. Acad. Sci. USA* 74:5463). DNA sequence determination may be performed by standard methods such as dideoxy chain termination technology and gel-electrophoresis, or by other methods such as by pyrosequencing (Biotage AB, Uppsala, Sweden). For example, DNA sequencing by dideoxy chain termination may be performed using unlabeled primers and labeled (e.g., fluorescent or radioactive) terminators. Alternatively, sequencing may be performed using labeled primers and unlabeled terminators. It is also contemplated that any of a variety of automated sequencing procedures may be utilized when performing the subject assays (see, for example *Biotechniques* (1995) 19:448), including sequencing by mass spectrometry (see, for example PCT publication WO 94/16101; Cohen et al. (1996) *Adv. Chromatogr.* 36:127-162; and Griffin et al. (1993) *Appl. Biochem. Biotechnol.* 38:141-159). The nucleic acid sequence of the DNA in the sample can be studied to determine whether a polymorphism associated with reduced MIF expression is present. It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In another embodiment, the presence of a polymorphism associated with reduced MIF expression is detected and/or determined using FISH. For example, a probe that specifically hybridizes to a sequence comprising a polymorphism associated with reduced MIF expression is hybridized to a subject's genomic DNA by FISH. FISH can be used, for example, in metaphase cells, to detect a deletion or repeat region in genomic DNA. Genomic DNA is denatured to separate the complimentary strands within the DNA double helix structure. The polynucleotide probe of the invention is then added to the denatured genomic DNA. In a specific embodiment, a probe that specifically hybridizes to a sequence comprising a polymorphism associated with reduced MIF expression is used. Accordingly, if a polymorphism associated with, reduced MIF expression is present, the probe will hybridize to the genomic DNA. The probe signal (e.g., fluorescence) can then be detected through a fluorescent microscope for the presence of absence of signal. The presence of signal, therefore, indicates the presence of a polymorphism associated with reduced MIF expression.

In another embodiment, the presence of a polymorphism associated with altered MIF expression is detected and/or determined by primer extension with DNA polymerase. In one embodiment, a polynucleotide primer of the invention hybridizes immediately adjacent to the polymorphism. A single base sequencing reaction using labeled dideoxynucleotide terminator may be used to detect the polymorphism. In one embodiment, the presence of a polymorphism associated with reduced MIF expression will result in, the incorporation of the labeled terminator, whereas the absence of a polymorphism associated with reduced MIF expression will not result in the incorporation of the terminator. In another embodiment, the dideoxynucleotides may be labeled (e.g., fluorescently, radioactively, chemically, etc.) and the polymorphism is detected by detecting the incorporation of the labeled dideoxynucleotides during or after primer extension. In another embodiment, a polynucleotide primer of the invention hybridizes specifically to a sequence comprising a polymorphism associated with reduced MIF expression. The presence of a polymorphism will result in primer extension, whereas the absence of a polymorphism will not result in primer extension. The primers and/or nucleotides may further include fluorescent, radioactive, or chemical probes. A primer labeled by primer extension may be detected by measuring the intensity of the extension product, such as by gel electrophoresis, mass spectrometry, or any other method for detecting fluorescent, radioactive, or chemical labels.

In another embodiment, the presence of a polymorphism associated with, altered MIF expression is detected and/or determined by ligation. In one embodiment, a polynucleotide primer hybridizes specifically to a sequence comprising a polymorphism associated with reduced MIF expression. A second polynucleotide that hybridizes to a region of the MIF geno immediately adjacent to the first primer is also provided. One, or both, of the polynucleotide primers may be fluorescently, radioactively, or chemically labeled. Ligation of the two polynucleotide primers will occur in the presence of DNA ligase if a polymorphism associated with reduced MIF expression is present. Ligation may be detected by gel electrophoresis, mass spectrometry, or by measuring the intensity of fluorescent, radioactive, or chemical labels.

For example, identification of a polymorphism can be carried out using an oligonucleotide ligation assay (OLA), as described, e.g., in U.S. Pat. No. 4,998,617 and in Landegren, U. et al. ((1988) *Science* 241:1077-1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) *Proc. Natl. Acad. Sci, USA* 87:8923-27). In this method, PCR is used to achieve the exponential amplification of target DNA, which is then detected using OLA.

Several techniques based on this OLA method have been developed and can be used to identify a polymorphism. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) *Nucleic Acids Res.* 24:3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of polymorphisms using a high throughput that leads to the production of two different colors.

In another embodiment, the presence of a polymorphism associated with altered MIF expression is detected and/or determined by single-base extension (SBE). For example, a fluorescently-labeled primer that is coupled with fluorescence resonance energy transfer (FRET) between the label of the added base and the label of the primer may be used. Typically, the method, such as that described by Chen et al., (*PNAS* 94:10756-61 (1997), incorporated herein by reference) uses a locus-specific polynucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide.

In certain embodiments, a polymorphism that is associated with altered MIF expression may be detected using single-strand conformation polymorphism analysis, which identifies base differences by alteration in electrophoretic migration of single stranded PCR products, as described in Orita et al., *Proc. Nat. Acad. Sci.* 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allele sequence immediately adjacent 3' to the polymorphic site is permitted to hybridize to a target molecule obtained from a subject. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to the sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al, (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779-7784 (1989); Sokolov, B. P., *Nucl. Acids Res.* 18:3671 (1990); Syvanen, A.-C., et al., *Genomics* 8:684-692 (1990); Kuppuswamy, M. N. et al., *Proc. Natl. Acad. Sci.* (*U.S.A.*) 88:1143-1147 (1991); Prezant, T. R. et al., *Hum. Mutat.* 1:159-164 (1992); Ugozzoli, L. et al., *GATA* 9:107-112 (1992); Nyren, P. et al., *Anal. Biochem,* 208:171-175 (1993)). These methods differ from GPA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., *Amer. J. Hum. Genet.* 52:46-59 (1993)).

For SNPs that produce premature termination of protein translation, the protein truncation test (PTT) offers an efficient diagnostic approach (Roest, et, al., (1993) *Hum. Mol. Genet.* 2:1719-21; van der Luijt, et. al., (1994) *Genomics* 20:1-4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Diagnostic procedures may also be performed in situ directly upon tissue sections (fixed and/or frozen) of subject tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, N.Y.).

In a further embodiment, protection from cleavage agents (such as a nuclease, hydroxylamine or osmium tetraoxide and with piperidine) can be used to detect mismatched bases in RNA/RNA or RNA/DNA or DNA/DNA heteroduplexes (Myers, et al. (1985) *Science* 230:1242). In general, the art technique of "mismatch cleavage" starts by providing heteroduplexes formed by hybridizing (labeled) RNA or DNA containing the one of the polymorphic alleles with the sample. The double-stranded duplexes are treated with an agent that cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; and Saleeba et al (1992) *Methods Enzymol.* 217:286295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662).

Commercial assays, such as the Taqman assay (Applied Biosystems, Foster City, Calif.), may also be used for genotyping a subject for the presence of a polymorphism that is associated with altered MIF expression. Genotyping and uses therefore are shown in U.S. Ser. Nos. 10/442,021, 10/013,598 (U.S. Patent Application Publication 20030036069), and U.S. Pat. Nos. 5,925,525, 6,268,141, 5,856,092, 6,267,152, 6,300,063, 6,525,185, 6,632,611, 5,858,659, 6,284,460, 6,361,947, 6,368,799, 6,673,579 and 6,333,179.

Polynucleotides used in any of the methods of the invention, including probes and primers, can be DNA or RNA or chimeric mixtures or derivatives or modified versions thereof, single-stranded or double-stranded. Polynucleotides of the invention can be modified at the base moiety, sugar moiety, or phosphate backbone, for example, to improve stability of the molecule, hybridization, etc. Polynucleotide probes of the invention may hybridize to a segment of target DNA such that the variation aligns with a central position of the probe, or the variation may align with a terminal position of the probe.

Standard instrumentation known to those skilled in the art can be used for the amplification and detection of amplified DNA. For example, a wide variety of instrumentation has been developed for carrying out nucleic acid amplifications, particularly PCR, e.g. U.S. Pat. No. 5,038,852 (computer-controlled thermal cycler); Wittwer et al., *Nucleic Acids Research*, 17: 4353-4357 (1989) (capillary tube PCR); U.S. Pat. No. 5,187,084 (air-based temperature control); Gamer et al, *Biotechniques*, 14: 112-115 (1993)(high-throughput PCR in 864-well plates); International application No. PCT/US93/04039 (PCR in micro-machined structures); European patent application No. 90301061.9 (publ. No. 0381501 A2)(disposable, single use PCR device), and the like. In certain embodiments, the invention described herein utilizes real-time PCR or other methods known in the art such as the Taqman assay.

MIF Polymorphism Detection Using Immobilized Probes

In certain embodiments, a polymorphism in the MIF gene that is associated with altered MIF expression may be detected using polynucleotide probes that have been immobilized on a solid support or substrate. Immobilized polynucleotide probes hybridize to a region of the MIF gene (including the promoter region of the MIF gene) that comprises a polymorphism that is associated with altered MIF expression. The present invention may employ any solid substrate known in the art, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098.

In a specific embodiment, the invention provides a solid support or substrate for simultaneously genotyping a microsatellite repeat and a SNP in the MIF gene (including the promoter region), Examples of solid supports and substrates include, without limitation, a nucleic acid probe array (e.g., a chip, a microarray, or an array), a nitrocellulose filter, a microwell, a bead, a sample tube, a microscope slide, a microfluidics device, and the like. The solid support may be made of various materials, including paper, cellulose, nylon, polystyrene, polycarbonate, plastics, glass, ceramic, stainless steel, or the like. The solid support may have a rigid or semi-rigid surface, and may be spherical (e.g., bead) or substantially planar (e.g., flat surface) with appropriate wells, raised regions, etched trenches, or the like. The solid support may also include a gel or matrix in which nucleic acids may be embedded or fibers or any solid support comprising bound nucleic acids. The solid support comprises at least two polynucleotide probes that are complementary to one or more polymorphisms associated with altered MIF expression. In a preferred embodiment, at least one of the probes detects a microsatellite repeat associated with altered MIF expression and at least one of the other probes detects a SNP associated with altered MIF expression. Hybridization to the polynucleotide probes can be detected using any detection method. In one embodiment, hybridization may be detected by the naked eye, without the aid of instruments for visualizing hybridization. Platforms for detection by the naked eye include thin-film technologies such as those described in Jenison et al., Expert Rev. Mol. Diagn. 6:89-99 (2006); Ostroff et al., Clinical Chemistry 45:1659-1664 (1999) and Zhong et al., PNAS 100:11559-11564 (2003), which are hereby incorporated by reference.

Thus, in a preferred embodiment, the invention provides the use of thin film technology to simultaneously genotype a microsatellite repeat and a SNP in the MIF gene. For example, in one embodiment, the invention provides the use of a thin film chip or microarray. Thin-film technology permits the visual detection of nucleic acid targets with the unaided eye. The assay is inexpensive, robust, highly specific, rapid and easy to use, thus permitting its implementation in rural settings with limited technology. See Jenison et al. (2006) Expert Rev. Mol. Diagn. 6:89-99.

Thin film technology is capable of generating a visual signal by the direct interaction of light with thin films formed on a solid surface (e.g., a silicon surface). The surface is constructed to be antireflective to specific wavelengths of light by the addition of antireflective coatings that create destructive interference. When light reflected from the surface-thin-film interface is out of phase with light reflected from the air-thin-film interlace, specific wavelengths of light are eliminated from the reflected light by destructive interference, creating a characteristic surface color. Optical thickness of the thin film, which is a function of both refractive index and physical thickness, determines which wavelengths of light are antireflective. Changes in the optical thickness of the thin film will result in a visible color change on the surface, once it is dried. This optical principle has been exploited to configure biologic assays on optical surfaces that transduce a thickness change into a surface color change that is a direct measure of interactions between target molecules in solution and capture molecules on the surface of the chip. The method is sensitive to thickness changes in the angstrom range, translating into highly sensitive detection of target molecules in very rapid assay formats.

By amplifying molecular interactions, the increased mass deposited on the surface of a thin film chip can be visually detected. Thin film formation can be accomplished by a variety of signal amplification techniques, such as by the enzymatic turnover of precipitating substrates. For the detection of nucleic acid sequences, thin film development may utilize, for example, the detection of biotin-labeled probes by binding of an antibiotin antibody conjugated to horseradish perixidasc (HRP). In the presence of a precipitating substrate for HRP, an enhanced molecular thin film is deposited onto the surface of the solid substrate. Control of the reflective properties to create, for example, a gold-colored surface is achieved by the coating of surfaces with optical layers of defined refractive index and thickness, using well-established semiconductor processes. Details of the preparation of the optically coated surfaces have been described previously. See, for example, Jenison et al. (2001). Biotech. 19:62-65. Briefly, the base surface of the chip is crystalline silicon, which provides a highly reflective, inert and molecularly flat surface to which the antireflective coating (silicon nitride) is applied by vapor deposition (e.g., to a thickness of 475 angstroms). An attachment layer, such as T-structure aminoalkyl polydimethy siloxane (TSPS) can be coated on the surface to provide better immobilization of biological materials, such as nucleic acid capture probes or antibodies.

In one embodiment, a solid support as described above (such as a chip or microarray) comprises at least one probe that hybridizes specifically to a sequence comprising a guanine or to a sequence comprising a cytosine at position −173 of the MIF promoter.

In another embodiment, a solid support as described above (such as a chip or micrarray) comprises at least one probe that hybridizes specifically to a sequence comprising a sequence selected from the group consisting of SEQ ID NO: 1 (CATTCATTCATTCATTCATT), SEQ ID NO: 2 (CATTCATTCATTCATTCATTCATT), SEQ ID NO: 3 (CATTCATTCATTCATTCATTCATTCATT), and SEQ ID NO: 4 (CATTCATTCATTCATTCATTCATTCATTCATT).

In another embodiment, a solid support as described above (such as a chip or microarray) comprises: (a) at least one probe that hybridizes specifically to a sequence comprising a guanine or a cytosine at position −173 of the MIF promoter; and, (b) at least one probe that hybridizes specifically to a sequence comprising a sequence selected from the group consisting of SEQ ID NO: 1, SEQ ID NO: 2, SEQ ID NO: 3, and SEQ ID NO: 4.

In another embodiment, a solid support as described above (such as a chip or microarray) comprises (a) a probe that hybridizes specifically to a sequence comprising a guanine at position −173 of the MIF promoter and another probe that hybridizes specifically to a sequence comprising a cytosine at position −173 of the MIF promoter.

In another embodiment, a solid support as described above (such as a chip or microarray) comprises: (a) a probe that hybridizes specifically to a sequence comprising SEQ ID NO: 1; (b) a probe that hybridizes specifically to a sequence comprising SEQ ID NO: 2; (c) a probe that hybridizes specifically to a sequence comprising SEQ ID NO: 3; and, (d) a probe that hybridizes specifically to a sequence comprising SEQ ID NO: 4.

In another embodiment, a solid support as described above (stich as a chip or microarray) comprises: (a) a probe that hybridizes specifically to a sequence comprising a guanine at position −173 of the MIF promoter; (b) a probe that hybridizes specifically to a sequence comprising a cytosine at position −173 of the MIF promoter; (c) a probe that hybridizes specifically to a sequence comprising SEQ ID NO; 1 (d) a probe that hybridizes specifically to a sequence comprising SEQ ID NO: 2; (e) a probe that hybridises specifically to a sequence comprising SEQ ID NO: 3; and, (f) a probe that hybridizes specifically to a sequence comprising SEQ ID NO: 4.

In one embodiment, the invention provides a method of determining the MIF genotype of a subject comprising contacting a solid substrate as disclosed herein with a sample obtained from the subject and determining the MIF genotype of the subject. The sample may be amplified prior to contacting the sample with the solid substrate disclosed herein. In one embodiment, the invention provides a method of determining the MIF genotype of a subject comprising: (a) amplifying a portion of the MIF gene comprising a polymorphism associated with altered MIF expression; (b) contacting a solid substrate as disclosed herein with the amplified portion; and, (c) determining whether the subject comprises a polymorphism associated with increased MIF expression or whether the subject comprises a polymorphism associated with reduced MIF expression, thereby determining the MIF genotype of the subject.

Other Genotyping Methods

Moreover, the genotyping methods disclosed herein can be substituted by the use of other methods that can establish whether a subject expresses MIF at reduced or increased levels. Such methods are therefore useful for identifying a subject particularly in need of a MIF agonist or susceptible to injury associated with reduced blood flow.

For example, the MIF protein levels can be measured in a subject and compared to the MIF protein levels in a subject with a genotype that is associated with reduced MIF expression (e.g., a guanine at position −173 of one or both alleles of the MIF promoter or five CATT repeats in the −794 region of one or both alleles of the MIF promoter). Alternatively, MIF protein levels can be measured in a subject and compared to the MIF protein levels in a subject with a genotype that is associated with increased MIF expression (e.g., a cytosine at position −173 of both alleles of the MIF promoter and/or six or more CATT repeats in the −794 region of both alleles of the MIF promoter).

Standard methods for measuring protein levels are known in the art. See, for example, *Current Protocols in Molecular Biology*, eds. Ausubel et al., John Wiley & Sons: 1992. For example, MIF protein levels can be measured by measuring the amount of light aborbance in a sample of the protein. Alternatively, MIF protein levels can be measured using an agent that binds to MIF protein, such as an antibody, an aptamer, a small molecule, another protein or an enzyme. Binding of the agent to MIF can be detected by the use of a signal (e.g., fluorescent, colorimetric, radioactive, chemical, or enzymatic), or may be detected by a chemical or enzymatic reaction. Other methods of measuring protein levels may include mass spectrometry, surface plasmon resonance or using protein chips.

The Use of MIF Agonists for Treatment

In one embodiment, the invention provides a method of increasing AMPK activity comprising administering to a subject a therapeutically effective amount of a MIF agonist. In some embodiments, the subject has a genotype that is associated with reduced MIF expression. In some embodiments, the subject has or is at risk of having a condition in which increased glucose uptake is desirable. Such conditions include hypoxia, especially hypoxia resulting from tissue ischemia. In various embodiments, the tissue ischemia is associated with acute coronary syndromes such as myocardial infarction, coronary revascularization (such as coronary bypass surgery and coronary angioplasty/stent placement), stroke, renal, retinal, mesenteric or limb ischemia due to vascular occlusion, organ transplant surgery (for maintaining viability and function of the transplanted organ), ischemia associated with vascular surgery, including hypothermic arrest and vascular cross-clamping.

In another embodiment, the condition is type 2 diabetes.

In one embodiment, a MIF agonist is administered to a subject prior to the observation of any symptoms indicating that increased AMPK activity or glucose uptake is desirable, such as signs of cell or tissue injury, loss of function or cell death. For example, a MIF agonist may be administered to an organ donor prior to organ removal. Alternatively, a MIF agonist may be administered as a prophylactic measure to prevent, e.g., ischemic injury or to patients at risk of experiencing decreased blood flow (e.g., patients at risk for ischemia). A MIF agonist also may be used to treat an organ prior to transplantation in a recipient.

The methods described herein may also comprise the administration of a MIF agonist with one or more additional therapeutic agents. In various embodiments, the therapeutic agents or agents that increase AMPK activity, stimulate blood flow, or increase glucose uptake. Such agents include but are not limited to metformin, rosiglitazone, pioglitazone, leptin, adiponectin and acadesine.

In other embodiments, a MIF agonist may be co-administered either separately or in the same dosage form with a fatty acid oxidation inhibitor. Such inhibitors are known in the art and include, e.g., ranolazine.

MIF Agonists

As described above any agent that mimics, activates, stimulates, potentiates or increases the biological activity of MIF can be used as a MIF agonist.

MIF agonists include isolated or recombinant nucleic acids that encode MIF proteins or fragments thereof; isolated or recombinant MIF polypeptides or fragments thereof; or other agents that mimic, activate, stimulate, potentiate or increase the biological activity of MIF. Examples of MIF agonists include, without limitation, agents that increase MIF mRNA or protein expression; agents that enhance CD44 mRNA or protein expression; agents that enhance CD74 mRNA or protein expression; agents that increase interaction between MIF, CD74 and CD44 (e.g., bivalent antibodies that bind two out of three of MIF, CD74 and CD44, fusion proteins with CDR combinations that bind two out of three of MIF, CD74 and CD44, and other agents that are identified by any of the screening methods described herein); agents that increase interaction between CD44 and CD74 (e.g., bivalent antibodies that bind CD74 and CD44, and other agents that are identified by any of the screening methods described herein); and agents that increase interaction between MIF and CD74 (e.g., bivalent antibodies that bind MIF and CD74, and other agents that are identified by any of the screening methods described herein). For example, agonist anti-CD74 or agonist anti-CD44 antibodies are useful as MIF pathway agonists. Other agents that may be used, comprising the use of agents that modulate the interaction between MIF, CD74 and CD44. Other agents that may be used to mimic, activate, stimulate, potentiate or increase the biological activity of MIF include, without limitation, drugs, metabolites, intermediates, cofactors, transition state analogs, ions, metals, toxins, natural and synthetic polymers (e.g., proteins, peptides, nucleic acids, polysaccharides, glycoproteins, hormones, receptors and cell surfaces such as cell walls and cell membranes, and antisense nucleic acids. Agents may also comprise alcohols, alkyl halides, amines, amides, esters, aldehydes, ethers and other classes of organic agents.

In a preferred embodiment, the MIF agonist is recombinant MIF.

In one embodiment, the D-dopachrome tautomerase (DDT) protein, or fragments thereof, is used to agonize the biogical activity of MIF. In another embodiment, an agonist of DDT is used to agonize the activity of MIF. An exemplary nucleotide sequence that encodes DDT is found in GenBauk Accession No. AH006997.

Aptamers and Small Molecules

Aptamers can also be used as MIF agonists. The present invention provides therapeutic aptamers that specifically bind to a MIF polypeptide or a polypeptide that affects MIF expression or MIF biological function, thereby agonizing activity of MIF.

In one embodiment, a MIF agonist may be an aptamer that binds to a MIF polypeptide and activates, stimulates or potentiates the activity of said MIF polypeptide. In one embodiment, a MIF agonist may be an aptamer that binds to a CD44 polypeptide and activates, stimulates or potentiates the activity of said CD44 polypeptide. In one embodiment, a MIF agonist may be an aptamer that binds to a CD74 polypeptide and activates, stimulates or potentiates the activity of said CD74 polypeptide.

An "aptamer" may be a nucleic acid molecule, such as RNA or DNA that is capable of binding to a specific molecule with high affinity and specificity (Ellington et al., *Nature* 346, 818-22 (1990); and Tuerk et al., *Science* 249, 505-10 (1990)). An aptamer will most typically have been obtained by in vitro selection for binding of a target molecule. For example, an aptamer that specifically binds to polypeptide important for the biological function of MIF (e.g., MIF, CD74 or CD44) can be obtained by in vitro selection from a pool of polynucleotides for binding to a polypeptide important for the biological function of MIF (e.g., MIF, CD74 or CD44). However, in vivo selection of an aptamer is also possible. Aptamers have specific binding regions which are capable of forming complexes with an intended target molecule in an environment wherein other substances in the same environment are not complexed to the nucleic acid. The specificity of the binding is defined in terms of the comparative dissociation constants (Kd) of the aptamer for its ligand (e.g., a MIF polypeptide, or a polypeptide important for the biological function of MIF such as CD74 or CD44) as compared to the dissociation constant of the aptamer for other materials in the environment or unrelated molecules in general. A ligand (e.g., a MIF, CD74 or CD44 polypeptide) is one which binds to the aptamer with greater affinity than to unrelated material. Typically, the Kd for the aptamer with respect to its ligand will be at least about 10-fold less than the Kd, for the aptamer with unrelated material or accompanying material in the environment. Even more preferably, the Kd will be at least about 50-fold less, more preferably at least about 100-fold less, and most preferably at least about 200-fold less. An aptamer will typically be between about 10 and about 300 nucleotides in length. More commonly, an aptamer will be between about 30 and about 100 nucleotides in length.

Methods for selecting aptamers specific for a target of interest are known in the art. For example, organic molecules, nucleotides, amino acids, polypeptides, target features on cell surfaces, ions, metals, salts, saccharides, have all been shown to be suitable for isolating aptamers that can specifically bind to the respective ligand. For instance, organic dyes such as Hoechst 33258 have been successfully used as target ligands for in vitro aptamer selections (Werstuck and Green, *Science* 282:296-298 (1998)). Other small organic molecules like dopamine, theophylline, sulforhodamine B, and cellobiose have also been used as ligand in the isolation of aptamers. Aptamers have also been isolated for antibiotics such us kanamycia A, lividomycin, tobramycin, neomycin B, viomycin, chloramphenicol and streptomycin. For a review of aptamers that recognize small molecules, see Famulok, *Science* 9:324-9 (1999).

An aptamer of the invention can be comprised entirely of RNA. In other embodiments of the invention, however, the aptamer can instead be comprised entirely of DNA, or partially of DNA, or partially of other nucleotide analogs. To specifically inhibit translation in vivo, RNA aptamers are preferred. Such RNA aptamers are preferably introduced into a cell as DNA that is transcribed into the RNA aptamer. Alternatively, an RNA aptamer itself can be introduced into a cell.

Aptanaers are typically developed to bind particular ligands by employing known in vivo or in vitro (most typically, in vitro) selection techniques known as SELEX (Ellington et al., *Nature* 346, 818-22 (1990); and Tuerk et al., *Science* 249, 505-10 (1990)). Methods of making aptamers are also described in, for example, U.S. Pat. No. 5,582,981, PCT Publication No. WO 00/20040, U.S. Pat. No. 5,270, 163, Lorsch and Szostak, *Biochemistry*, 33:973 (1994), Mannironi et al., *Biochemistry* 36:9726 (1997), Blind, *Proc. Nat'l. Acad. Sci. USA* 96:3606-3610 (1999), Huizenga and Szostak, *Biochemistry*, 34:656-665 (1995), PCT Publication Nos. WO 99/54506, WO 99/27133, WO 97/42317 and U.S. Pat. No. 5,756,291.

Generally, in their most basic form, in vitro selection techniques for identifying aptarners involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 15-25 nucleotide long region of defined sequence useful for the binding of PCR primers. The oligonucleotide pool is amplified using standard PCR techniques, although any means that will allow faithful, efficient amplification of selected nucleic acid sequences can be employed. The DNA pool is then in vitro transcribed to produce RNA transcripts. The RNA transcripts may then be subjected to affinity chromatography, although any protocol which will allow selection of nucleic acids based on their ability to bind specifically to another molecule (e.g., a protein or any target molecule) may be used. In the case of affinity chromatography, the transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand. Once an aptamer sequence has been successfully identified, the aptamer may be further optimized by performing additional rounds of selection starting from a pool of oligonucleotides comprising the mutagenized aptamer sequence. For use in the present invention, the aptarner is preferably selected for ligand binding in the presence of salt concentrations and temperatures which mimic normal physiological conditions.

The unique nature of the in vitro selection process allows for the isolation of a suitable aptamer that binds a desired ligand despite a complete dearth of prior knowledge as to what type of structure might bind the desired ligand.

The association constant for the aptamer and associated ligand is preferably such that the ligand functions to bind to the aptamer and have the desired effect at the concentration of ligand obtained upon administration of the ligand. For in vivo use, for example, the association constant should be such that binding occurs well below the concentration of ligand that can be achieved in the serum or other tissue. Preferably, the required ligand concentration for in vivo use is also below that which could have undesired effects on the organism.

The present invention also provides small molecules and antibodies that specifically bind to a polypeptide important for the biological function of MIF (e.g., MIF, CD74 or CD44), thereby agonizing the biological function of MIF. Examples of small molecules include, without limitation, drugs, metabolites, intermediates, cofactors, transition state analogs, ions, metals, toxins and natural and synthetic polymers (e.g., proteins, peptides, nucleic acids, polysaccharides, glycoproteins, hormones, receptors and cell surfaces such as cell walls and cell membranes).

Antibodies, Antibody Fragments and Other Fusion Proteins

Antibodies or fragments thereof specifically reactive with a polypeptide that affects the expression or biological function of MIF may be used as MIF agonists. Antibodies or fragments thereof directed, for example, to MIF, CD44, CD74, and/or combinations thereof, may be agonists of the expression or biological function of MIF.

In certain embodiments, an antibody or fragment thereof that is specifically reactive with a MIF polypeptide may be used as a MIF agonist to increase or activate the activity or a MIF polypeptide. In one embodiment, a MIF agonist is an antibody, such as a bivalent antibody or a fragment thereof, that is able to bind MIF. In another embodiment, a MIF agonist is an antibody, such as a bivalent antibody or a fragment thereof, that is able to bind MIF and CD44. In another embodiment, a MIF agonist is an antibody, such as a bivalent antibody or a fragment thereof, that is able to CD44 and CD74. In another embodiment, a MIF agonist is an antibody, such as a bivalent antibody or a fragment thereof, that is able to bind MIF and CD74

Methods of making antibodies are well known in the art. For example, by using immunogens derived from a MIF polypeptide or a polypeptide that affects the expression or biological function of MIF, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the MIF polypeptide, an antigenic fragment which is capable of eliciting an antibody response, or a fusion protein. Such mammals can also be immunized with an immunogenic form of a polypeptide that affects the expression or biological function of MIF. Techniques for conferring immunogenicity on a protein or peptide include conjugation to carriers or other techniques well known in the art. An immunogenic portion of a MIF polypeptide or a polypeptide that affects the expression or biological function of MIF can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of a MIF polypeptide or a polypeptide that affects the expression or biological function of MIF, antisera can be obtained and, if desired, polyclonal antibodies can be isolated from the serums. To produce monoclonal antibodies, antibody-producing cells (lymphocytes) can be harvested from an immunized animal and fused by standard somatic cell fusion procedures with immortalizing cells such as myeloma cells to yield hybridoma cells, Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the BBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a MIF polypeptide or a polypeptide that affects the expression or biological function of MIF. Monoclonal antibodies can be isolated from a culture comprising such hybridoma cells.

The term "antibody" as used herein is intended to include fragments thereof which are also specifically reactive with a MIF polypeptide or a polypeptide that affects the expression or biological function of MIF. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the invention is a monoclonal antibody, and in certain embodiments, the invention makes available methods for generating novel antibodies that bind specifically to MIF polypeptides or to polypeptides that affect the expression or biological function of MIF. For example, a method for generating a monoclonal antibody that binds specifically to a MIF polypeptide, or to a polypeptide that affects the expression or biological function of MIF, may comprise administering to a mouse an amount of an immunogenic composition comprising the MIF polypeptide or the polypeptide that affects the expression or biological function of MIF, effective to stimulate a detectable immune response, obtaining antibody-producing cells (e.g., cells from the spleen) from the mouse and fusing the antibody-producing cells with myelomia cells to obtain antibody-producing hybridonaas, and testing the antibody-producing hybridomas to identify a hybridoma that produces a monocolonal antibody that binds specifically to the MIF polypeptide or the polypeptide that affects the expression or biological function of MIF. Once obtained, a hybridoma can be propagated in a cell culture, optionally in culture conditions where hybridoma-derived cells produce the monoclonal antibody that binds specifically to the MIF polypeptide or the polypeptide that affects the expression or biological function of MIF. The monoclonal antibody may be purified from the cell culture.

The term "specifically reactive with" as used in reference to an antibody is intended to mean, as is generally understood in the art, that the antibody is sufficiently selective between the antigen of interest (e.g., a MIF polypeptide or a polypeptide that affects the expression or biological function of MIF) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody: antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include BLISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays, and immunohistochemistry.

General Information Relating to Methods of Treatment Using MIF Agonists

The methods described herein for increasing AMPK activity may be used prophylactically. Thus, in one embodiment, a composition comprising a MIF agonist is administered in an amount and dose that is sufficient to delay, slow, or prevent tissue injury associated with hypoxia including tissue ischemia.

MIF agonists may be formulated with a pharmaceutically acceptable carrier. For example, a MIF agonist can be administered alone or as a component of a pharmaceutical formulation (therapeutic composition). The MIF agonist may be formulated for administration in any convenient way for use in human medicine.

In certain embodiments, the therapeutic methods of the invention include administering the composition topically, systemically, or locally. For example, therapeutic compositions of the invention may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions described herein may be formulated as part of an implant or device. When administered, the therapeutic composition for use in this invention is in a pyrogen-free, physiologically acceptable form. Further, the composition may be encapsulated or injected in a viscous form for delivery to the site where the target cells are present. Techniques and formulations generally may be found in Remington's Pharmaceutical Sciences, Meade Publishing Co., Easton, Pa. In addition to MIF agonists, therapeutically useful agents may optionally be included in any of the compositions described herein. Furthermore, therapeutically useful agents may, alternatively or additionally, be administered simultaneously or sequentially with a MIF agonist according to the methods of the invention.

In certain embodiments, compositions comprising a MIF agonist can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more compositions, comprising a MIF agonist may be mixed with one or more pharmaceutically acceptable carriers, such as sodium citrate or dicalcium phosphate, and/or any of the following: (1) fillers or extenders, such us starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quatemary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers, Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oil, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required. The ointments, pastes, creams and gels may contain, in addition to a MIF agonist, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a MIF agonist, excipients such as lactose, talc, silicie acid, aluminum hydroxide, calcium silicates, and polyimide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenterat administration may comprise a MIF agonist in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising MIF agonist may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments, the present invention also provides gene therapy for the in vivo production of a MIF agonist. Such therapy would achieve its therapeutic effect by introduction of a polynucleotide sequence that encodes a MIF agonist into cells or tissues to increase MIF expression and/or activity. Delivery of MIF agonist polynucleotide sequences can be achieved using a recombinant expression vector such as a chinerio virus or a colloidal dispersion system. Targeted liposomes may also be used for the therapeutic delivery of MIF polynucleotide sequences.

Various viral vectors which can be utilized for gene therapy as taught herein include adenovirus, herpes virus, vaccinia, or an RNA virus such as a retrovirus. A retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made targct-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the polynucleotide that encodes the MIF agonist.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for polynucleotides that encode MIF agonists is a colloidal dispersion system. Colloidal dispersion systems include macromolecule complexes, nanocapsules, microspheres, heads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see, e.g., Fraley, et al., *Trends Biochem. Sci.* 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposornes depend on pH, ionic strength, and the presence of divalent cations.

Examples of lipids usoful in liposome production include phosphatidyl compounds, such as phosphatidylglycerol, phosphatidylchotine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

Moreover, a composition comprising a MIF agonist can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral packages, the pharmaceutical preparation can comprise one or more cells which produce the gene delivery system. In the ease of the latter, methods of introducing the viral packaging cells may be provided by, for example, rechargeable or biodegradable devices. Various slow release polymeric devices have been developed and tested in vivo in recent years for the controlled delivery of drugs, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

A person of ordinary skill in the art, such as a physician, is able to determine the required amount to treat the subject. It is understood that the dosage regimen will be determined for an individual, taking into consideration, for example, various factors that modify the action of a MIF agonist, the severity of the condition associated with hypoxia or tissue ischemia, route of administration, and characteristics unique to the individual, such as age, weight, and size. In one embodiment, the dosage can range from about 1.0 ng/kg to about 100 mg/kg body weight of the subject.

In certain embodiments, a composition comprising a MIF agonist for topical, systemic or local administration can be administered in a range from about 0.001% to about 3.0% (weight per volume or weight per weight), or from about 0.001% to about 0.01%, from about 0.01% to about 0.025%, from about 0.025% to about 0.05%, from about 0.05% to about 0.1%, from about 0.1% to about 0.25%, from about 0.25% to about 1.0%, from about 1.0% to about 2.0%, or from about 2.0% to greater than 3.0%, i.e., about 3.0% to about 10.0% or greater. In a specific embodiment, a composition comprising a MIF agonist is administered in strange from about 0.25% to about 3.0%.

In certain embodiments, a composition comprising a MIF agonist is administered in a range of from about 1 ng/ml to about 1 g/ml, or from about 1 ng/ml to about 10 ng/ml, from about 10 ng/ml to about 100 ng/ml, from about 100 ng/ml to about 1 mg/ml, from about 1 mg/ml to about 10 mg/ml, from about 10 mg/ml to about 100 mg/ml or from about 100 mg/ml to about 1 g/ml. In certain embodiments, a composition comprising a MIF agonist is administered in a range of from about 40 ng/ml to about 100 ng/ml.

The volume of composition administered according to the methods described herein is also dependent on factors such as the mode of administration, quantity of the MIF agonist, age and weight of the patient, and type and severity of the disease being treated. For example, if administered orally as a liquid, the liquid volume comprising a composition comprising a MIF agonist may be from about 0.5 milliliters to about 2.0 milliliters, from about 2.0 milliliters to about 5.0 milliliters, from about 5.0 milliliters to about 10.0 milliliters, or from about 10.0 milliliters to about 50.0 milliliters. If administered by injection, the liquid volume comprising a composition comprising a MIF agonist may be from about 5.0 microliters to about 50 microliters, from about 50 microliters to about 250 microliters, from about 250 microliters to about 1 milliliter, from about 1 milliliter to about 5 milliliters, from about 5 milliliters to about 25 milliliters, from about 25 milliliters to about 100 milliliters, or from about 100 milliliters to about 1 liter.

The dose can be delivered continuously, or at periodic intervals (e.g., on one or more separate occasions). Desired time intervals of multiple doses of a particular composition can be determined without undue experimentation by one skilled in the art. For example, the compound may be delivered hourly, daily, weekly, monthly, yearly (e.g. in a time release form) or as a one time delivery. If administered orally or topically, such a preparation can be administered 1 to 6 times per day for a period of 1-4 weeks, 1-3 months, 3-6 months, 6-12 months, 1-2 years, or more, up to the lifetime of the patient. If administered by injection, MIF agonistic compositions can be delivered one or more times periodically throughout the life of a patient. For example, a MIF agonist composition can be delivered once per year, once every 6-12 months, once every 3-6 months, once every 1-3 months, once every 1-4 weeks, one or more times per day. Alternatively, more frequent administration may be desirable for certain conditions or disorders. If administered by an implant or device, MIF agonist compositions can be administered one time, or one or more times periodically throughout the lifetime of the patient as necessary.

Samples used in the methods described herein may comprise cells from the eye, ear, nose, throat, teeth, tongue, epidermis, epithellum, blood, tears, saliva, mucus, urinary tract, urine, muscle, cartilage, skin, or any other tissue or bodily fluid from which sufficient DNA, RNA or protein can be obtained. In certain embodiments, samples used in the methods described herein comprise cells from a tracheal aspirate or nasal washing.

The sample should be sufficiently processed to render the DNA, RNA or protein that is present in the sample available for assaying in the methods described herein. For example, samples may be processed such that DNA from the sample is available for amplification or for hybridization to another polynucleotide. The processed samples may be crude lysates where available DNA, RNA or protein is not purified from other cellular material. Alternatively, samples may be processed to isolate the available DNA, RNA or protein from one or more contaminants that are present in its natural source. Samples may be processed by any means known in the art that renders DNA, RNA or protein available for assaying in the methods described herein. Methods for processing samples may include, without limitation, mechanical, chemical, or molecular means of lysing and/or purifying cells and cell lysates. Processing methods may include, for example, ion-exchange chromatography, size exclusion chromatography, affinity chromatography, hydrophobic interaction chromatography, gel filtration chromatography, ultrafiltration, electrophoresis, and immunoaffinity purification with antibodies specific for particular epitopes of the polypeptide Screening Assays In certain aspects, the present invention relates to the use of MIF, and/or CD44 and/or CD74 to identify agents that are agonists of AMPK activity. Agents identified through this screening can be tested in coils and tissues to assess their ability to modulate the biological activity of AMPK in vivo or in vitro. In certain aspects, these agents can further be tested in animal models to assess their ability to modulate the biological activity of AMPK in vivo. The compounds identified in these methods can be used to increase AMPK activity as described herein. The methods described herein are based on the discovery that CD44 functionally interacts with MIF (Meyer-Siegler et al., *BMC Cancer*, 4:34 (2004) and Meyer-Siegler et al., *J Urol.*, 173:615-620 (2005)).

In one embodiment, the invention provides a method of identifying potential agonists of the biological activity of AMPK, comprising: (a) contacting a CD44 polypeptide or a portion thereof, with a CD74 polypeptide, or portion thereof; in the presence and absence of a candidate agent; and (b) comparing the interaction of the CD44 and CD74 polypeptides in the presence of said candidate agent with the interaction in the absence of said candidate agent. A candidate agent that enhances the interaction of the CD44 polypeptide and the CD74 polypeptide is thus identified as a potential agonist of AMPK biological function.

In another embodiment, the invention provides a method of identifying potential agonists of the biological activity of AMPK, comprising: (a) contacting a CD44 polypeptide or a portion thereof, with a MIF polypeptide, or a portion thereof; and a CD74 polypeptide or a portion thereof, in the presence and absence of a candidate agent; and, (b) comparing the interaction of the CD44 polypeptide or portion thereof and the MIF and CD74 polypeptides or portions thereof in the presence of said candidate agent with the interaction in the absence of said candidate agent. A candidate agent that enhances the interaction of the CD44 polypeptide and the MIF and CD74 polypeptides is thus identified as a potential agonist of AMPK biological function.

The interaction between the agent and the subject polypeptide (e.g., CD44, CD74, MIF, and/or MIF/CD74) may be covalent or non-covalent. For example, such interaction can be identified at the protein level using in vitro biochemical methods, including photo-crosslinking, radiolabeled ligand binding, and affinity chromatography (Jakoby W B et al., 1974, *Methods in Enzymology* 46:1). In certain cases, the agents may be screened in a mechanism based assay, such as an assay to detect agents which bind to the subject polypeptide (e.g., CD44, CD74, MIF, and/or MIF/CD74). This may include a solid phase or fluid phase binding event. Alternatively, the gene or genes encoding one or more of the subject polypeptides can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound agents may be detected usually using colorimetric or fluorescence or surface plasmon resonance.

In certain embodiments, high-throughput screening of agents can be carried out to identify agents that affect the biological function of AMPK. A variety of assay formats will suffice and, in light of the present disclosure, those not expressly described herein will nevertheless be comprehended by one of ordinary skill in the art. As described herein, the test agents of the invention may be created by any combinatorial chemical method. Alternatively, the subject agents may be naturally occurring biomolecules synthesized in vivo or in vitro. Agents to be tested for their ability to act as modulators of the biological function of AMPK can be produced, for example, by bacteria, yeast, plants or other organisms (e.g., natural products), produced chemically (e.g., small molecules; including peptidomimetics), or produced recombinantly. Test agents contemplated by the present invention include non-peptidyl organic molecules, peptides, polypeptides, polysaccharides, peptidomimeties, sugars, hormones, and nucleic acid molecules.

The candidate agents of the invention can be provided as single, discrete entities, or provided in libraries of greater complexity, such as made by combinatorial chemistry. The agents can comprise, for example, drugs, metabolites, intermediates, cofactors, transition state analogs, ions, metals, toxins and natural and synthetic polymers (e.g., proteins, peptides, nucleic acids, polysaccharides, glycoproteins, hormones, receptors and cell surfaces such as cell walls and cell membranes. Agents may also comprise alcohols, alkyl halides, amines, amides, esters, aldehydes, ethers and other classes of organic agents. Presentation of candidate agents to the test system can be in either an isolated form or as mixtures of agents, especially in initial screening steps. Optionally, the agents may be derivatized with other agents and have derivatizing groups that facilitate isolation of the agents. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many screening programs which test libraries of agents and natural extracts, high throughput assays are desirable in order to maximize the number of agents surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test agent. Moreover, the effects of cellular toxicity or bioavailability of the test agent can be generally ignored in the in vitro system, the assay instead being focused primarily on the effect of the agent on the molecular target.

Kits

Also provided heroin are kits, e.g., kits for therapeutic purposes or kits for genotyping subjects to identify a reduced MIF expression genotype. In one embodiment, a kit comprises at least one container means having disposed therein reagents for genotyping a subject for the presence of a polymorphism associated with reduced MIF expression. For illustrative purposes, genotyping reagents may include polynucleotide probes or primers, or solid substrates such as chips or microarrays that are capable of detecting whether a polymorphism associated with reduced MIF expression is present. For use in a kit, polynucleotides may be any of a variety of natural and/or synthetic compositions, or chimeric mixtures thereof, such as synthetic polynucleotides, restriction fragments, cDNAs, synthetic peptide nucleic acids (PNAs), and the like. The assay kit and method may also employ labeled polynucleotides to allow ease of identification in the assays. Examples of labels which may be employed include radiolabels, enzymes, fluorescent compounds, streptavidin, avidin, biotin, magnetic moieties, metal binding moieties, antigen, enzymatic or antibody moieties, and the like. The kit may optionally comprise a label and/or instructions for use.

The kit may, optionally, also include DNA sampling means. DNA sampling means are well known to one of skill in the art and can include, but not be limited to substrates, such as filter papers, the AmpliCard™ (University of Sheffield, Sheffield, England S10 2JF; Tarlow, J W, et al., *J. of Invest. Demotol.* 103:387-389 (1994)) and the like; DNA purification reagents such as Nuoleon™ kits, lysis buffers, proteinase solutions and the like; PCR reagents, such as 10× reaction buffers, thermostable polymerase, dNTPs, and the like; and allele detection means such as the Hinfl restriction enzyme, allele specific oligonucleotides, degenerate oligonucleotide primers for nested PCR from dried blood. Other kit reagents may include enzymes, buffers, small molecules, nucleotides or their analogs, labels (e.g., fluorescent, radioactive, colorimetric, enzymatic or chemical) and/or co-factors as required for the genotyping assay.

In another embodiment, a kit comprises at least one container means having disposed therein a premeasured dose of one or more MIF agonists. A kit may optionally comprise devices for contacting cells with the MIF agonists and a label and/or instructions for use. Devices include syringes, dispensers, stents and other devices for introducing a MIF agonist into a subject (e.g, the blood vessel of a subject) or applying it to the skin of a subject. Kits may also include packaging material such as, but not limited to, ice, dry ice, styrofoam, foam, plastic, cellophane, shrink wrap, bubble wrap, paper, cardboard, starch peanuts, twist ties, metal clips, metal cans, drierite, glass, and rubber (see products available from www.papermart.com. for examples of packaging material).

The practice of the present methods will employ, unless otherwise indicated, conventional techniques of cell biology, cell culture, molecular biology, transgenic biology, microbiology, recombinant DNA, and immunology, which are within the skill of the art. Such techniques axe explained fully in the literature. See, for example, Molecular Cloning: A Laboratory Manual, Cold Spring Harbor Laboratory (2001); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and, Handbook Of Experimental Immunology, Volumes I-IV (D. M. Weir and C. C. Blackwell, eds., 1986).

EXAMPLES

The following examples are for illustrative purposes and are not intended to be limiting in any way.

Example 1

MIF Stimulation of AMP-Activated Protein Kinase During Hypoxia

A. Induction of MIF Expression and AMPK Activation by Hypoxia

Initially, to investigate MIF's role in the stimulation of the AMPK signaling pathway during hypoxia, we conducted experiments in isolated rat heart left ventricular papillary muscles.

Briefly, rat heart anterior and posterior left ventricular papillary muscles (3-5 mg) were equilibrated in oxygenated Dulbecco's phosphate-buffered saline (PBS) containing 1 mM $MgCl_2$ 1 nM $CaCl_2$, glucose, and 1% BSA. Unless otherwise noted, 100% oxygen flowed continuously through sealed muscle incubation containers while muscles were kept in an oscillating water bath at 37° C., and experiments began after a 15 minute equilibration period in these conditions. During incubations designed to examine the effects of hypoxia, muscles were transferred to incubation containers gassed with $N_2$ for 30 minutes. In incubations with rMIF (0-800 ng/ml), anti-MIF blocking antibody (100 μg/ml), and/or non-immune rabbit IgG (100 μg/ml); Sigma, USA), these compounds were added for 30-120 minutes. At the end of experiments, muscles were freeze clamped and stored in liquid nitrogen until further analysis, unless otherwise specified.

AMPK alpha isoform-specific kinase activity was measured via $[^{32}P]ATP$ (New England Nuclear, Boston, Mass.) incorporation into the synthetic SAMS peptide after AMPK antibody immunoisolation (α1 or α2; Santa Cruz Biotechnology, Santa Cruz, Calif.) coupled to protein G/A sepharose beads.

Figure 1C:
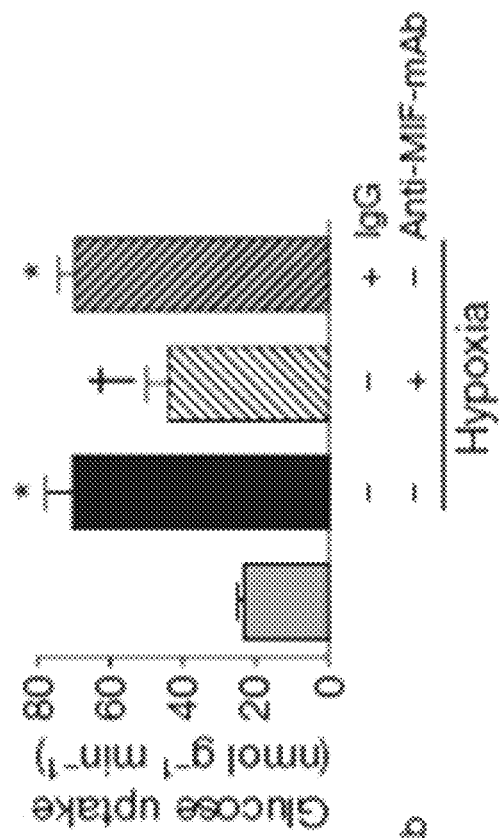
Figure 1D:
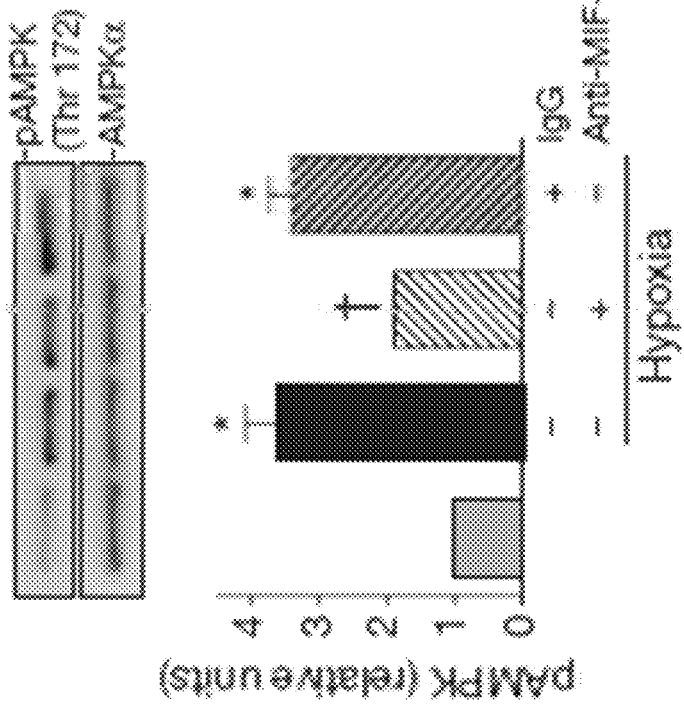

Hypoxia stimulated MIF release into the incubation media, as measured by ELISA (FIG. 11B), and led to AMPK alpha subunit Thr172 phosphorylation and increased activity of both AMPK alpha catalytic, isoforms, α1 and α2 (FIG. 1A). Thirty minutes of hypoxia caused a 2-fold increase in MIF production, Pre-treatment of the heart muscles with anti-MIF immune-neutralizing antibody reduced the hypoxic activation of AMPK by 67% (FIG. 1C). In contrast, control experiments showed no inhibition of AMPK activation by pre-incubation with non-immune rabbit IgG. Hypoxic activation of glucose transport was also inhibited by the addition of anti-MIF, while non-immune IgG had no inhibitory effect (FIG. 1D).

B. Activation of AMPK by Recombinant Human MIF

To further support MIF's role in modulating the AMPK pathway, we added recombinant human MIF (rMIF) to intact normoxic heart muscles. Papillary muscles were isolated as above. Following pre-incubation with rMIF, 2-deoxy-$[1-^3H]$ glucose (1 μCi/ml was added during the final 60 minutes of the experiment to measure the rates of glucose transport and phosphorylation. To assess the ability of MIF immuno-neutralization to block hypoxia-stimulated glucose uptake, papillary muscles were pre-incubated with anti-MIF immuno-neutralizing antibody or rabbit IgG followed by incubation in hypoxic media containing 2-deoxy-$[1-^3H]$ glucose. To correct for the muscle extracellular space and extracellular deoxyglucose, $[U-^{14}C]$ mannitol (0.1 μCi/ml) was also added. After incubations, muscles were washed in ice-cold PBS, blotted dry, weighed, solubillzed in Soluene-350 (Packard Instrument, Meriden, Conn.) and counted by liquid scintillation.

Figures 1E, 1F:
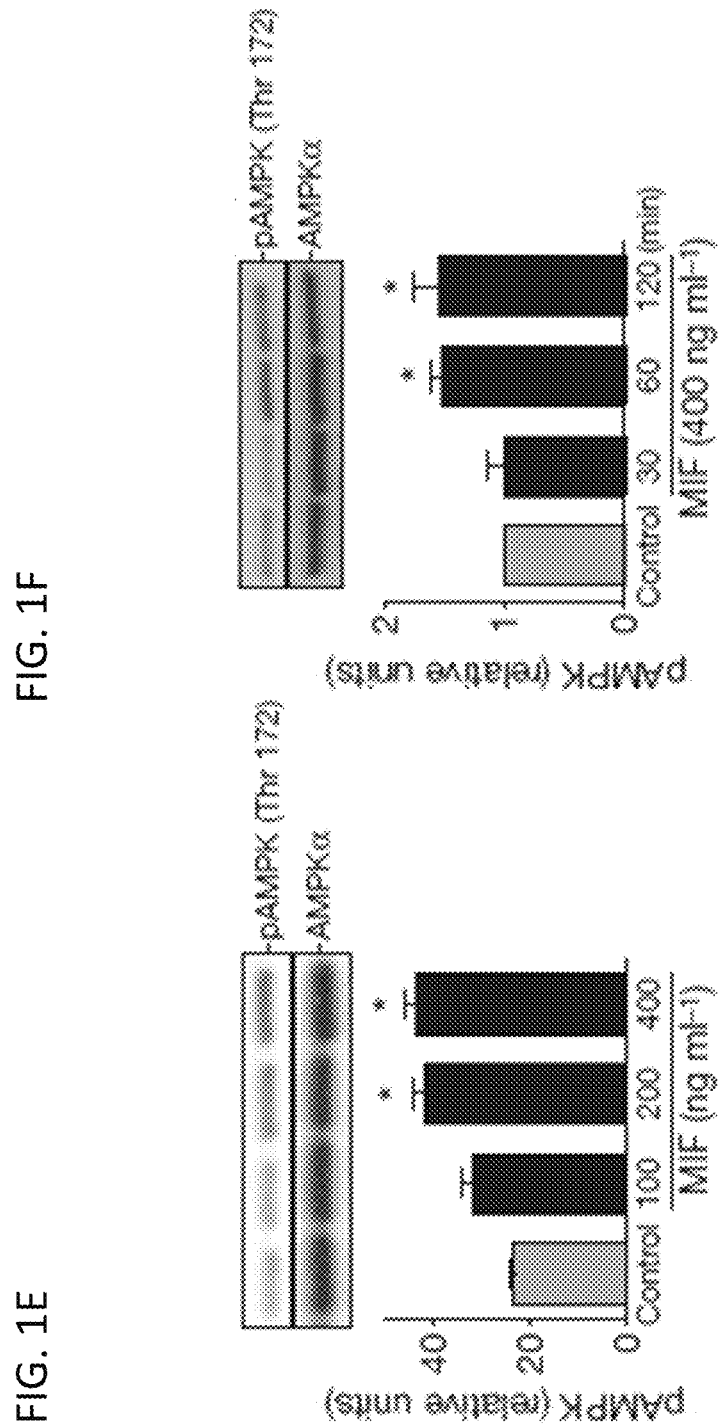
Figure 1H:
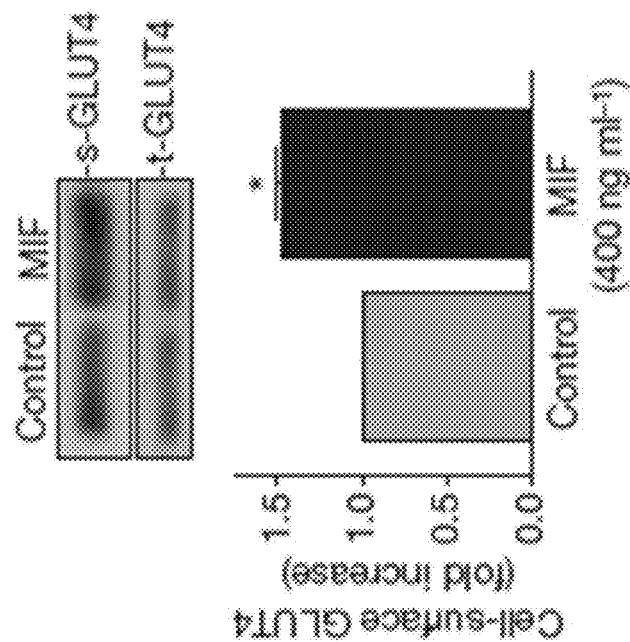
Figure 1G:
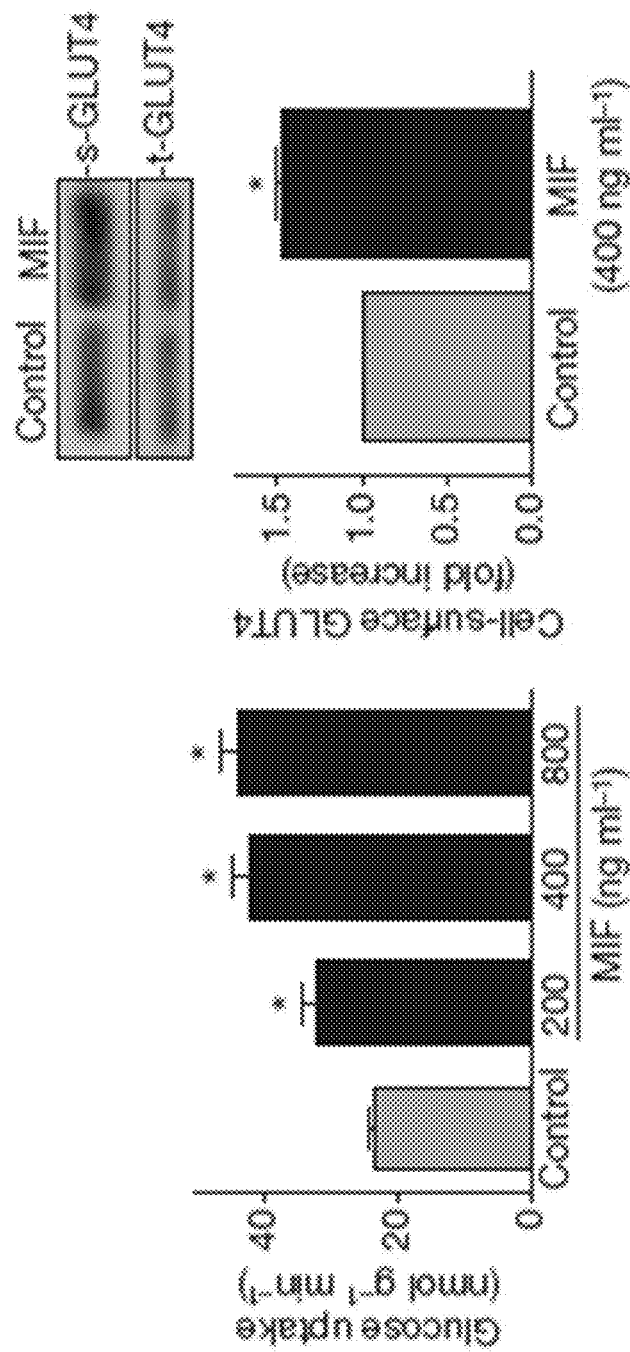

MIF caused a time- and dose-dependent increase in AMPK Thr172 phosphorylation, with maximal AMPK activation (1.5-2.0 fold increase) seen with 400 ng/ml rMIF incubated for 60 minutes (FIGS. 1E and 1F). Likewise, parallel downstream AMPK pathway activation was evident with an increase in glucose uptake after the addition of rMIF to normoxic heart muscles (FIG. 1G).

Glucose uptake is primarily mediated by the glucose transporter, GLUT4, and AMPK-stimulation of glucose transport is due to the translocation of GLUT4 vesicles to the cell surface, where GLUT4 is physiologically active (Sun et al., *Circulation* 89, 793 (1994); Young et al., *Circulation* 95, 415 (1997)). Thus, we assessed the cell-surface GLUT4 content of heart muscles after incubation with rMIF, utilizing a cell-membrane impermeant biotinylated glucose transporter photolabel (bio-LC-ATB-BGPA).

Incubation with rMIF increased cell-surface GLUT4 in the heart muscles (FIG. 1H), providing a mechanism for increased glucose uptake during MIF incubation. To measure cell surface GLUT4, papillary muscles were rinsed in ice-cold glucose-free Krobs-Henseleit buffer (KHB) and incubated in cold KHB containing 400 μmol/Lbio-LC-ATB-BGPA (4,4-O-[2-[2-[2-[2-[2-[6-(biotinylamino)hexanolyl]-amino]ethoxy]ethoxyl]-ethoxy]-4-1-azi-2,2,2-trifluoro-ethyl)benzoyl]amino-1,3-propanediyl]bis-D-glucose).

Following cross-linking of bio-LC-ATB-BGPA to cell-surface glucose transporters by UV irradiation, cell surfact GLUT4 was isolated on streptavidin-agarose (Pierce Biotechnology, Rockford, Ill.), identified by immunoblotting and quantified by densitometry.

Thus, these data taken together provide evidence that MIF is released in heart muscle in response to hypoxia, leading to activation of AMPK, stimulation of GLUT4 translocation and glucose uptake.

Example 2

MIF Stimulates AMP-Activated Protein Kinase in Ischemia

We next examined the role of MIF in AMPK signaling in ischemia utilizing isolated mouse heart perfused with a crystalloid buffer to eliminate the potential contribution of MIF from circulating immune cells or monocytes during ischemia.

A. Determination of MIF Expression in Ischemia

Figure 2A:
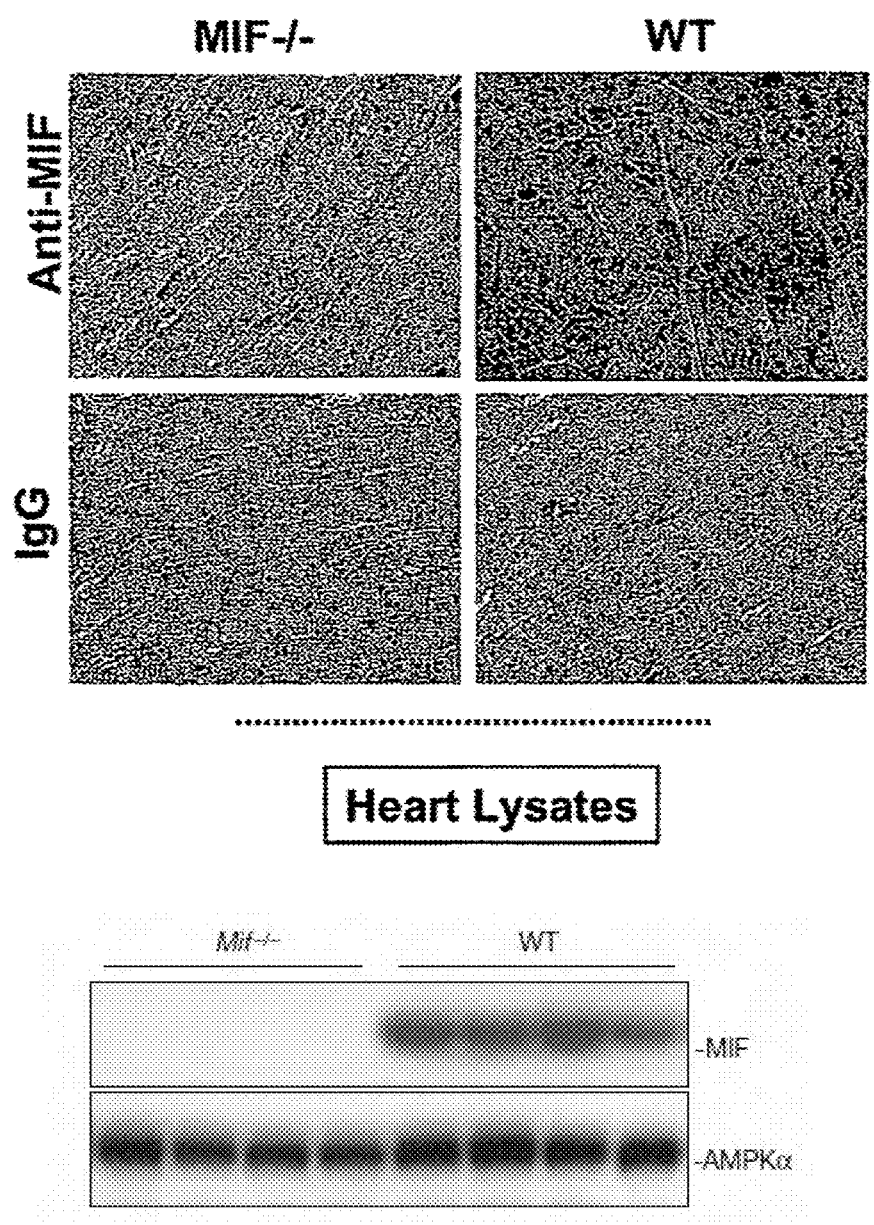
FIGS. 2A and 2B show cardiomyocyte MIF localization and ischemic cardieac MIF release.

Immunoblotting of whole-heart lysates showed high-level MIF protein expression in the heart, and immunohistochemistry of heart sections demonstrated cardiomyocyte-predominant MIF staining in hearts from wild-type mice following control perfusions (FIG. 2A). Male MIF −/− mice were compared to age-matched wild-type BALB/c controls. Mouse hearts were retrogradely perfused in the Langendorff mode with modified KHB buffer containing 7 mmol/L glucose, 1.0 mmol/L oleate, 1% BSA, and a low fasting concentration of insulin (10 µU/mL). Hearts were perfused for 30 minutes at a flow of 4 mL/min, followed by either: 20 minutes of global ischemia, 20 minutes of global ischemia followed by 30 minutes of reperfusion, or control perfusion of the appropriate duration at continued baseline flow. Cardiac function was measured by a fluid-filled balloon inserted into the left ventricular cavity, connected to a Millar transducer (Millar Instruments, Houston, Tex.) and acquired via an ADInstruments PowerLab system with Chart v.5.2.2 software (ADInstuments, Colorado Springs, Colo.). Hearts were freeze-clamped in liquid nitrogen at the end of the perfusions unless otherwise noted. For immunohistochemistry, hearts were fixed with 4% formalin after perfusions and infused via the aortic cannula followed by immersion, paraffin embedded, and 3 µm sections cut with a tissue microtome. Sections were immunostained using a DakoCytomation EnVision+ System-HRP (DAB) (DakoCytomation, Carpinteria, Calif.) at room temperature alter d-parafinlzation with xylene and ethanol. Endogenous peroxidases were blocked using Dako Peroxidase Blook, followed by blocking of non-specific antibody binding sites with 10% bovine scrum albumin. Primary antibody incubation were preliminarily performed at multiple dilutions to establish optimum signabbackgrotmd recovery, leading to use of a final primary antibody dilution of 1:1000 incubated for 4 hours. Secondary antibody incubation with labeled polymer-HRP anti-rabbit antibody was followed by developing with DAB and counterstaining, with hematoxylin. Negative controls for each heart included use of non-specific rabbit IgG (Santa Cruz, Santa Cruz, Calif.) and secondary antibody alone. Specificity of the anti-MIF was demonstrated by lack of staining of sections from MIF−/− tissues. All sections were processed simultaneously, developed for identical periods, and analyzed by light microscopy after dehydration with ethanol and xylene and mounting under coverslips.

Immunoblots were performed according to standard methods known in the art. See, for example, Li et al., *Am. J. Physiol Endocrinol Metab* 287, E384 (2004) and Baron et al., *Circ Res* (Jan. 13, 2005). Heart homogenate proteins were combined with Laemmli sample buffer prior to resolution by SDS-PAGE, transferred onto polyvinylidene difluoride membranes, immunoblotted, detected with enhanced chemiluminesence, and quantified by densitometry.

Figure 2B:
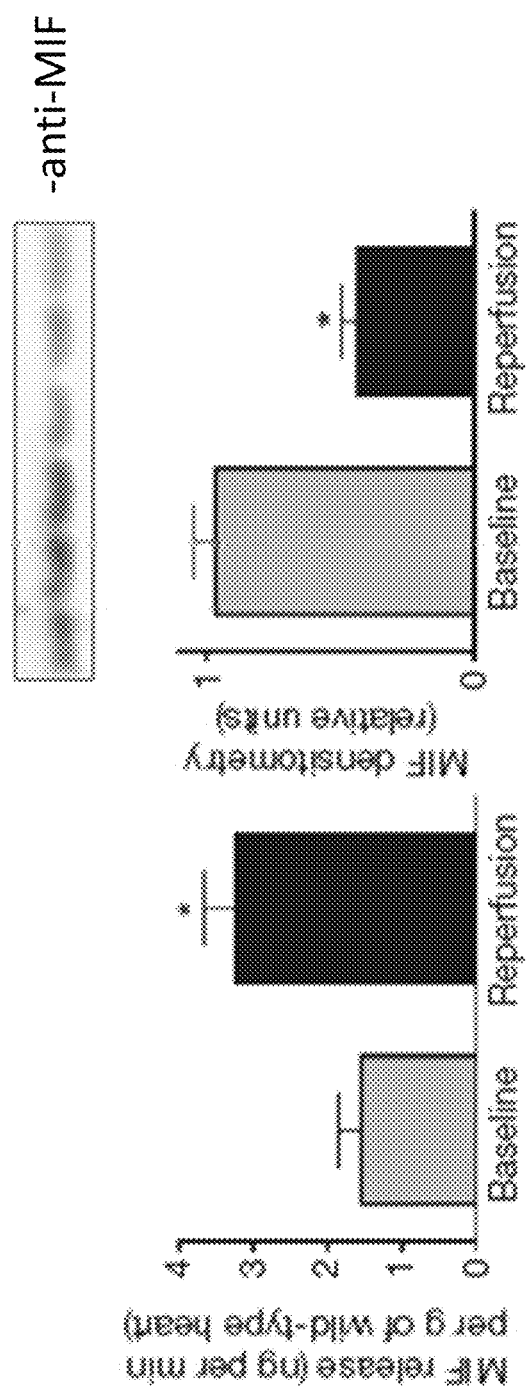

During cardiac perfusion in the Langendorff mode, MIF was released from hearts into the coronary venous effluent, but heart MIF release was increased 2-fold during reperfusion after ischemia (3.2±0.43 vs. 1.5±0.3 ng/min/g, P=0.01) which correlated with a significant decrease in heart homogenate MIF levels (0.96±0.15 vs. 0.43±0.010 relative units, P=0.03) (FIG. 2B). Increased MIF release from the heart during reperfusion after this brief period of ischemia was not associated with evidence of myocardial necrosis, based the results of vital staining and creatine kinase measurement on the coronary effluent.

B. AMPK Signaling in the Presence and Absence of MIF

To determine the role of MIF in isehemic cardiac AMPK activation, we examined AMPK signaling in hearts from transgenic MIF−/− mice compared to wild-type (WT) controls. The generation of germline MIF−/− has been previously described (Bozza et al., *J Exp Med* 189, 341 (1999)). No MIF was detected by immunohistochemistry or immunoblotting in MIF−/− hearts (FIG. 2A). The cardiac phenotype of the MIF−/− mice was characterized. Normal cardiac chamber sizes and function were found by echocardiography. There were no evident histological abnormalities, and normal heart weight:body weight ratio and normal expression of total AMPK, GLUT1, and GLUT4 were found (FIG. 5). MIF−/− and WT hearts were perfused with a mixed-substrate buffer in the Langendorff mode and subjected to 15 minutes of global, no-flow ischemia.

Figure 3A:
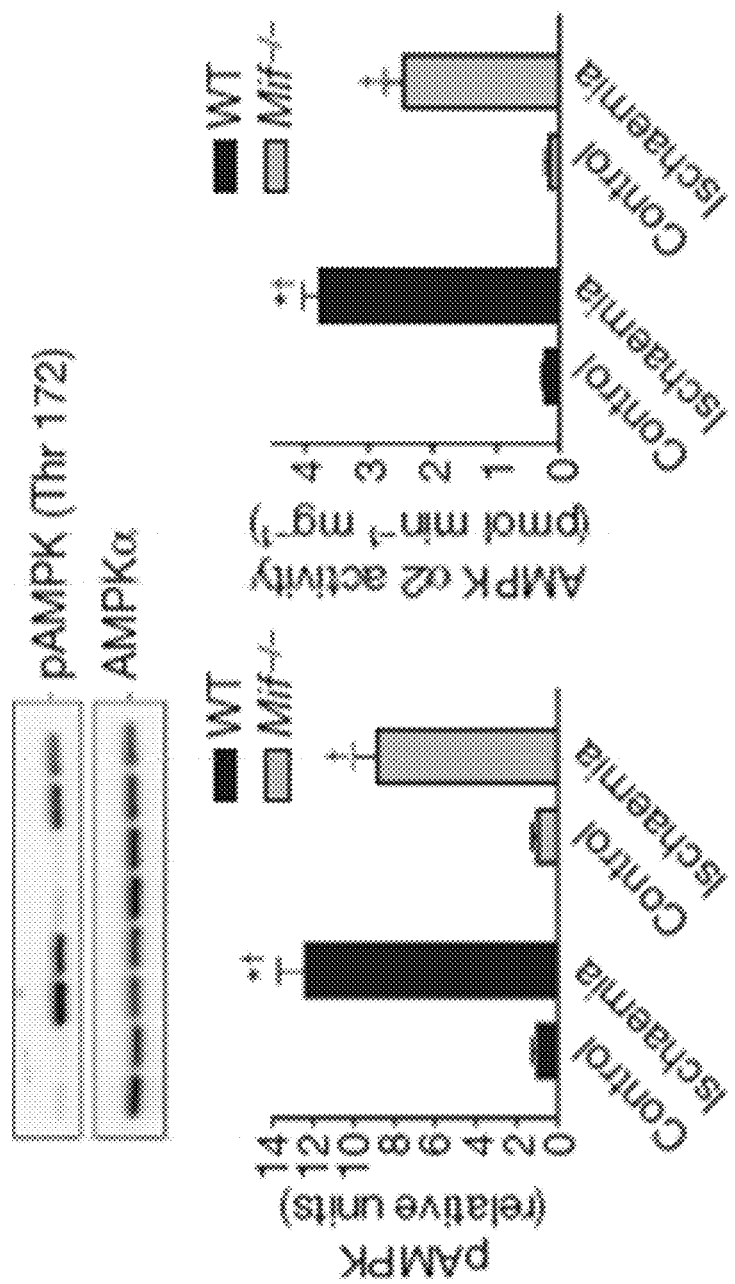
FIGS. 3A-3C show ischemic AMPK activation, glucose uptake, and post-ischemic cardiac function in isolated perfused MIF−/− hearts.
Figure 3B:
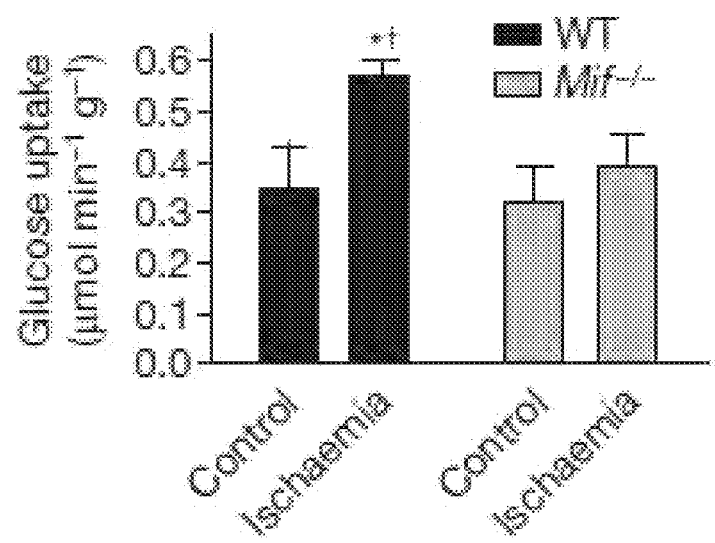
Figure 6:
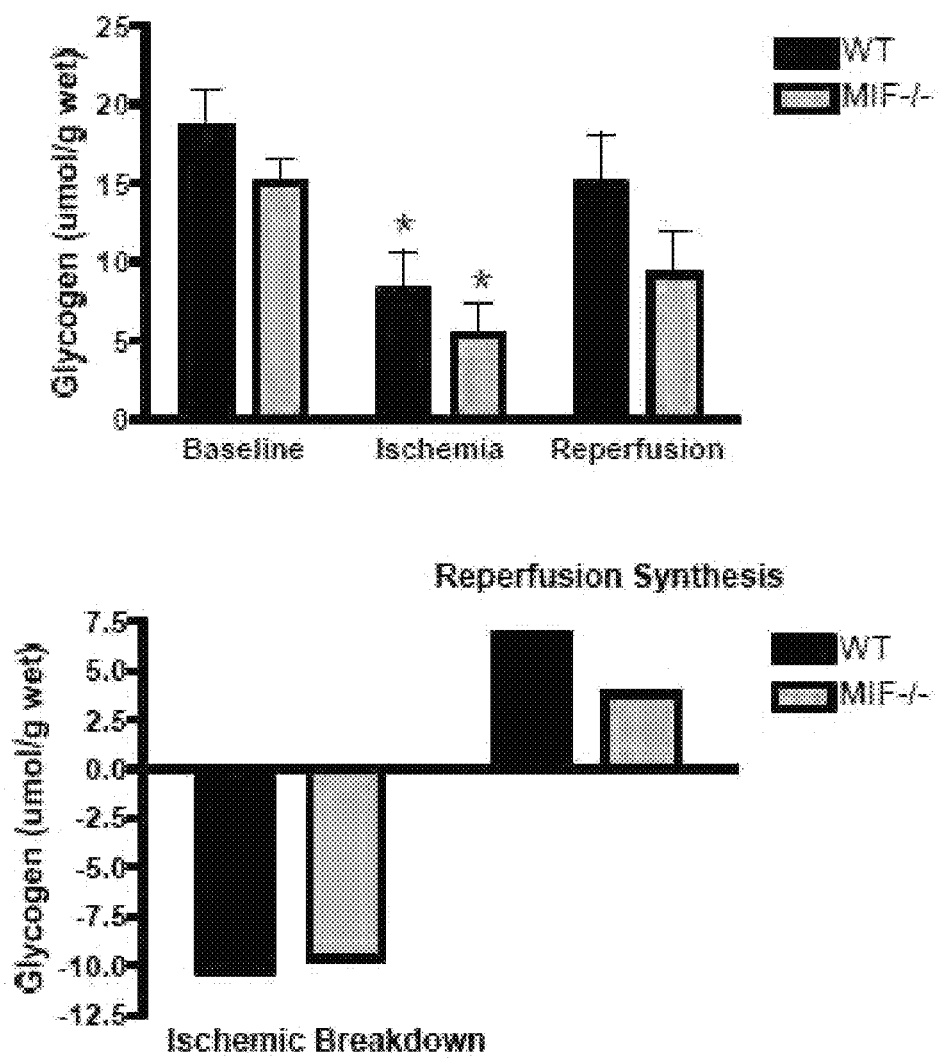
FIG. 6 shows cardiac glycogen content in WT and MIF−/− hearts. (top) Cardiac glycogen content measured using the amyloglucosidase method alter KOH digestion after control perfusion (baseline), 15 minutes of ischemia, or 15 minutes of ischemia/30 minutes of reperfusion (n=3-4 per group, *P<0.03 versus baseline). (bottom) Calculated ischemic glycogen breakdown (baseline minus ischemia) and reperfusion glycogen synthesis (reperfusion minus ischemia) from group means above.

Following ischemia, AMPK phosphorylation and activity were decreased in the MIF−/− hearts (FIG. 3A). This defect in AMPK, signaling translated to a defect in glucose uptake following ischemia in the MIF−/− hearts (FIG. 3B). Rates of glucose uptake were similar in WT and MIF−/− hearts during control perfusions. During post-ischemic reperfusion, however, stimulation of glucose uptake was significantly blunted in MIF−/− compared to WT hearts (P=0.04). Consistent with impaired glucose uptake during ischemic reperfusion, MIF−/− hearts also had diminished glycogen synthesis compared to WT hearts, despite similar calculated amount of ischemic glycogen breakdown (FIG. 6).

Figure 3C:
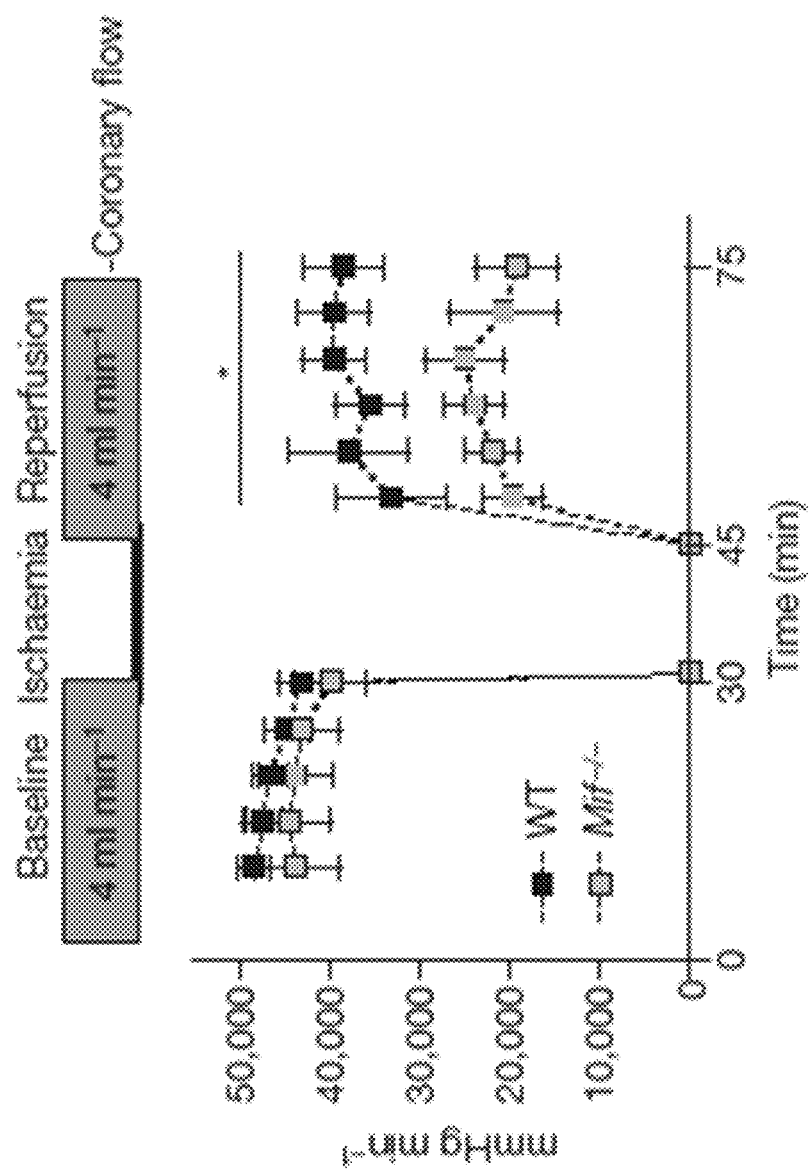
Figure 7:
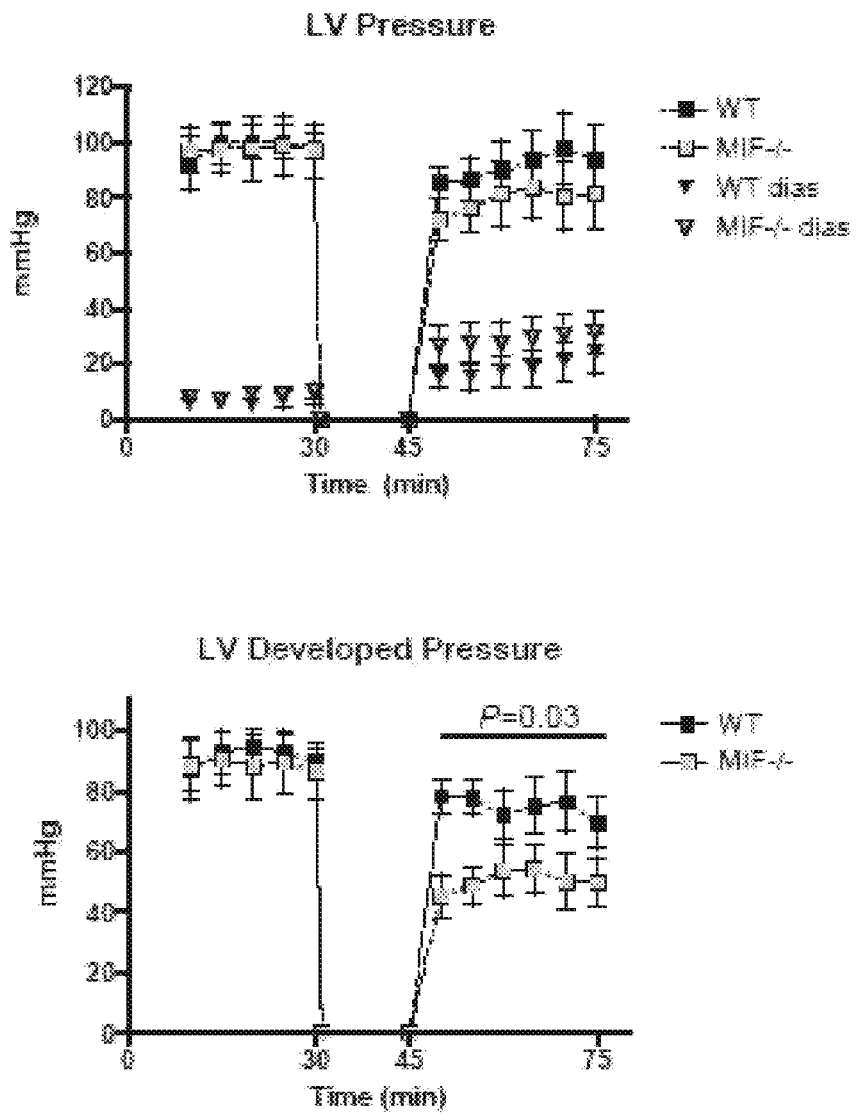
FIG. 7 shows loft ventricular systolic and diastolic pressure (top) and +dp/dt (bottom) in isolated WT and MIF−/− hearts during perfusion in the Langendorff mode. Left ventricular balloon volume initially set to achieve a diastolic pressure of 5 mmHg during baseline perfusion (n=10-12 per genotype, P=0.0001 WT vs. MIF−/− during reperfusion, ANOVA).

Defective AMPK signaling in the MIF−/− hearts impaired their ischemic tolerance. Baseline cardiac function was similar in WT and MIF−/− hearts perfused with mixed substrate buffer (FIG. 3C). However, when reperfused following ischemia, MIF−/− hearts had impaired recovery of cardiac function compared to WT controls, as evidenced by reduced left ventricular rate-pressure product (FIG. 3C), as well as depressed left ventricular developed pressure and contractility (+dp/dt) (FIG. 7). On average, MIF−/− hearts recovered 51±6.1% of their pre-ischemic cardiac function, while WT hearts recovered 81±8.7% (P=0.03). These results support the contention that MIF activation of AMPK during ischemia/reperfusion promotes early adaptive metabolic responses in the heart, while also elucidating a new physiologic action for MIF in the heart.

Example 3

Effect of Polymorphism in the Human MIF Promoter on MIF Secretion and AMPK Activation We also examined the effect of polymorphisms in the human MIF promoter on functional differences in MIF secretion and cellular AMPK activation. Early passage human dermal fibroblasts were subjected to hypoxia treatment and the degree of AMPK activation was assessed in relation to their MIF promoter polymorphism alleles.

To isolate human fibroblasts, human foreskin samples were obtained from the Yale Human Cell Resource Center (Department of Dermatology) in accordance with the Yale Human Investigations Committee. Fibroblasts were cultured in DMEM supplemented with 10% fetal bovine serum (FBS), penicillin (100 IU/ml) and streptomycin (100 µg/ml) at 37° C. Cells were studied at 80% confluence, and on the day prior to experiments, culture media was changed to DMEM with 1% FBS. Early passage fibroblasts were either subjected to 9 hours of hypoxia by incubation in an air-tight chamber gassed with 95% nitrogen/5% $CO_2$ or control incubation in room air.

Figure 4A:
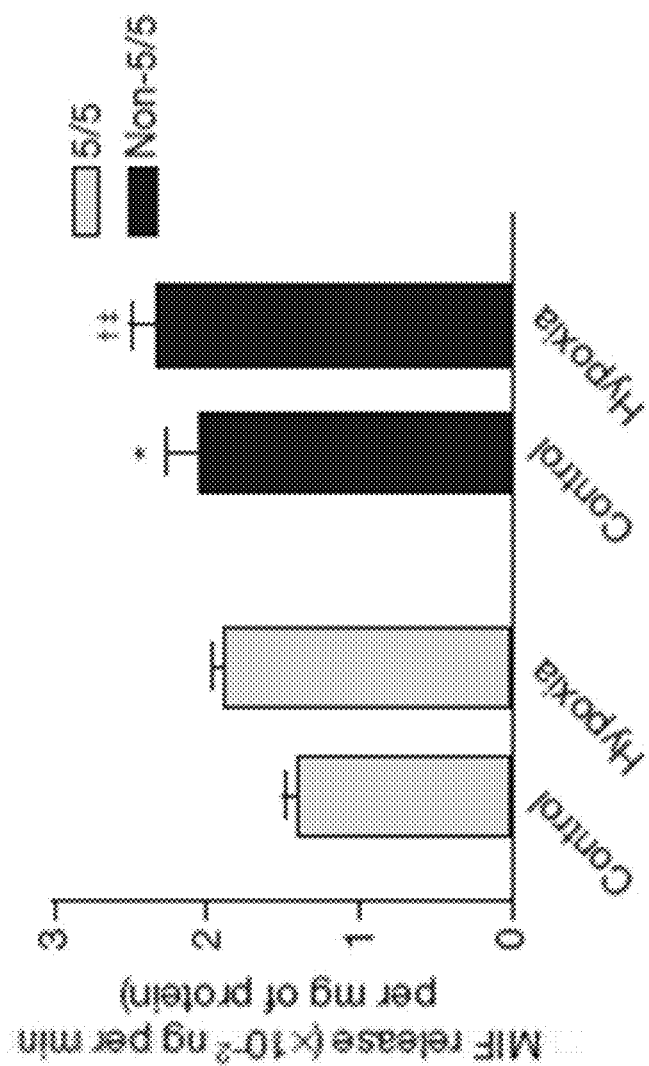
FIGS. 4A and 4B show AMPK activation correlation with MIF promoter genotype in hypoxic human fibroblasts.
Figure 4B:
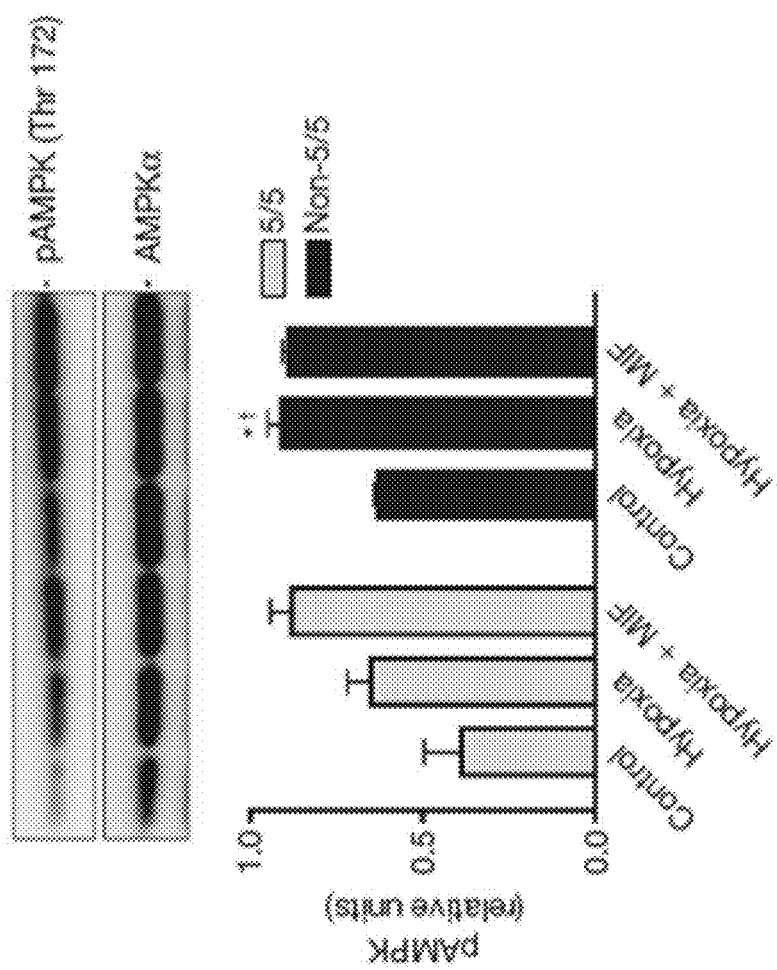

Three of seven specimens carried two 5-CATT alleles ("5/5" genotype) with the remainder having at least one 6, 7, or 8-CATT repeat alleles ("non-5/5" genotype). Fibroblasts with the non-5/5 genotype had significantly greater MIF release into the culture media both basally (P=0.03), as well as after hypoxia (P=0.05), compared to 5/5 genotype cells (FIG. 4A). We found that greater MIF release from the non-5/5 genotype fibroblasts was associated with significantly increased hypoxic AMPK phosphorylation compared to fibroblasts with the 5/5 MIF promoter genotype (FIG. 4B).

To confirm that relative MIF deficiency was responsible for impaired hypoxic AMPK activation in the low-expressing 5/5 genotype fibroblasts, we investigated the effect of adding human rMIF (10 ng/ml) to the culture media during hypoxic incubation. The addition of rMIF "rescued" hypoxic AMPK signaling in the 5/5 genotype fibroblasts, increasing hypoxic AMPK phosphorylation to levels that were equivalent to the non-5/5 fibroblasts, but had no additional effect on AMPK phosphorylation in hypoxic non-5/5 fibroblasts (FIG. 4B). These results demonstrate differential MIF release governed by a common polymorphism in the human MIF gene promoter that has consequences in stress signaling, specifically modulating hypoxic AMPK signaling. Taken together with the above results implicating MIF in the activation of AMPK in ischemia, these data indicate that common polymorphisms in the MIF promoter gene may be used as indicators of susceptibility to ischemic injury, particularly in patients with coronary artery disease.

Statistical data were expressed as means±standard deviation. A value of P<0.05 was considered significant. Significance was tested by Student 2-tail t tests or 2-way repeated measures ANOVA with Bonferroni correction for multiple comparisons when appropriate, using GraphPad Prism 4.02.

A rabbit polyclonal antibody raised to pure rMIF was used for immunohistochemistry, and a rabbit anti-rat MIF antibody (Tony Pines Biolabs, Houston, Tex.) was used for immunoblotting. Rabbit monoclonal anti-AMPK p-Thr$^{172}$ (Cell Signaling, Beverly, Mass.), rabbit anti-AMPK alpha (Cell Signaling, Beverly, Mass.), rabbit anti-GLUT4, and HRP-conjugated streptavidin (Pierce, Rockford, Ill.) were used for respective immunoblosts as described.

Animals were housed in accordance with guidelines from the American Association for Laboratory Animal Care. All procedures were approved by the Yale University Animal Care and Use Committee. All animals were housed in a 12-hour light/dark cycle and allowed standard chow and water ad libitum. Male Sprague-Dawley rats weighing 250-275 g were purchased from Charles River Laboratories. Wild-type male BALB/c mice (age 10-16 weeks) were purchased from Charles River Laboratories and compared to MIF-/- mice (generation N8) bred at the Yale Animal Resources Center on the BALB/c genetic background.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In ease of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nib.gov).

What is claimed is:

1. A method of increasing uptake of AMPK-mediated glucose into a cell, comprising administering a MIF agonist to a subject in need thereof,
   wherein the MIF agonist increases the uptake of AMPK-mediated glucose into the cell; and
   wherein the subject has a condition in which increased AMPK activity is desirable selected from the group consisting of hypoxia, ischemia, and type 2 diabetes.

2. A method of increasing AMPK-mediated glycolysis in a cell, comprising administering a MIF agonist to a subject in need thereof,
   wherein the MIF agonist increases the AMPK-mediated glycolysis in the cell; and
   wherein the subject has a condition in which increased AMPK activity is desirable selected from the group consisting of: hypoxia, ischemia, and type 2 diabetes.

* * * * *